US011406685B2

(12) United States Patent
Aizman et al.

(10) Patent No.: US 11,406,685 B2
(45) Date of Patent: *Aug. 9, 2022

(54) METHODS AND COMPOSITIONS FOR STIMULATION OF CELL PROLIFERATION AND PROVISION OF BIOLOGICALLY ACTIVE MIXTURES OF FGF2 ISOFORMS

(71) Applicant: SanBio, Inc., Mountain View, CA (US)

(72) Inventors: Irina Aizman, Mountain View, CA (US); Damien Bates, Menlo Park, CA (US)

(73) Assignee: SanBio, Inc., Mountain View, CA (US)

( * ) Notice: Subject to any disclaimer, the term of this patent is extended or adjusted under 35 U.S.C. 154(b) by 441 days.

This patent is subject to a terminal disclaimer.

(21) Appl. No.: 16/438,813

(22) Filed: Jun. 12, 2019

(65) Prior Publication Data

US 2019/0290730 A1 Sep. 26, 2019

Related U.S. Application Data

(63) Continuation of application No. 15/710,528, filed on Sep. 20, 2017, now Pat. No. 10,363,285, which is a continuation of application No. PCT/US2016/025559, filed on Apr. 1, 2016.

(60) Provisional application No. 62/204,776, filed on Aug. 13, 2015, provisional application No. 62/178,190, filed on Apr. 1, 2015.

(51) Int. Cl.
| *A61K 38/18* | (2006.01) |
| *A61K 35/28* | (2015.01) |
| *C12N 5/0793* | (2010.01) |
| *C12N 5/0797* | (2010.01) |
| *A61K 35/33* | (2015.01) |

(52) U.S. Cl.
CPC .......... *A61K 38/1825* (2013.01); *A61K 35/28* (2013.01); *A61K 35/33* (2013.01); *C12N 5/0619* (2013.01); *C12N 5/0623* (2013.01); *C12N 2501/115* (2013.01); *C12N 2502/1352* (2013.01)

(58) Field of Classification Search
None
See application file for complete search history.

(56) References Cited

U.S. PATENT DOCUMENTS

| 5,486,359 | A | 1/1996 | Caplan et al. |
| 7,682,825 | B2 | 3/2010 | Dezawa et al. |
| 8,092,792 | B2 | 1/2012 | Dezawa et al. |
| 10,363,285 | B2 | 7/2019 | Aizman et al. |
| 2003/0003090 | A1 | 1/2003 | Prockop et al. |
| 2008/0220085 | A1* | 9/2008 | Johnstone ............. A61K 35/35 424/574 |
| 2010/0266554 | A1 | 10/2010 | Mori et al. |
| 2011/0020291 | A1 | 1/2011 | Banerjee et al. |
| 2011/0229442 | A1 | 9/2011 | Dezawa |
| 2012/0225130 | A1 | 9/2012 | Yarmush et al. |
| 2013/0210000 | A1 | 8/2013 | Aizman et al. |
| 2014/0186316 | A1 | 7/2014 | Borlongan et al. |
| 2015/0231052 | A1 | 8/2015 | Ling et al. |
| 2018/0036378 | A1 | 2/2018 | Aizman et al. |

FOREIGN PATENT DOCUMENTS

| JP | 2005-206559 | 8/2005 |
| WO | WO 2005/100552 | 10/2005 |
| WO | WO 2009/023251 | 2/2009 |
| WO | WO 2011/054100 | 5/2011 |
| WO | WO 2016/161290 | 10/2016 |

OTHER PUBLICATIONS

Aizman et al. "Quantitative Microplate Assay for Studying Mesenchymal Stromal Cellinduced Neuropoiesis," Stem Cells Translational Medicine, 2.:223-232 (2013).
Aizman et al., "Cell Injury-Induced Release of Fibroblast Growth Factor 2: Relevance to Intracerebral Mesenchymal Stromal Cell Transplantations", Stem Cells and Development, vol. 24, No. 14, pp. 1623-1634, Jul. 15, 2015, XP55513292, NL ISSN: 1547-3287, DOI: 10.1089/scd.2015.0083.
Aizman et al., "Comparison of the neuropoietic activity of gene-modified versus parental mesenchymal stromal cells and the identification of soluble and extracellular matrix-related neuropoietic mediators," Stem Cell Res Ther, 5(1):29:1-15 (Feb. 26, 2014).
Aizman et al., "Extracellular Matrix Produced By Bone Marrow Stromal Cells and By Their Derivatne, SB623 Cells, Supports Neural Cell Growth," J Neurosci. Res. 87(14):3198-3206 (2009).
Artavanis-Tsakonas et al., "Notch Signaling," Science, 268(5208):225-232 (1995).
Bang et al., "Autologous mesenchymal stem cell transplantation in stroke patients," Ann Neurol., 57:874-882, 2005.
Benavente et al., :Subcellular distribution and mitogenic effect of basic fibroblast growth factor in mesenchymal uncommitted stem cells, Growth Factors, 21:87-94, 2003.
Benzaquen et al., "Terminal complement proteins C5b-9 release basic fibroblast growth factor and platelet-derived growth factor from endothelial cells," J Exp Med., 179:985-992, 1994.
Bogousslavsky et al., "Fiblast (Trafermin) in Acute Stroke Group: Fiblast (trafermin) in acute stroke: results of the European-Australian phase II/III safety and efficacy trial," Cerebrovasc Dis., 14:239-251, 2002.
Brumm et al., "An arterial spin labeling investigation of cerebral blood flow deficits in chronic stroke survivors," Neuroimage, 51:995-1005, 2010.
Brunner et al., "Phospholipase C release of basic fibroblast growth factor from human bone marrow cultures as a biologically active complex with a phosphatidylinositol-anchored heparan sulfate proteoglycan," J Cell Biol., 114:1275-1283, 1991.

(Continued)

*Primary Examiner* — Daniel C Gamett
(74) *Attorney, Agent, or Firm* — Levine Bagade Han LLP

(57) ABSTRACT

Disclosed herein are methods and compositions for providing mixtures of FGF2 isoforms that are biologically active. The biological activities include, but are not limited to, stimulation of proliferation of neural precursor cells, stimulation of proliferation of endothelial cells, stimulation of development of neural precursor cells, and stimulation of development of astrocytes.

29 Claims, 13 Drawing Sheets

(56) References Cited

OTHER PUBLICATIONS

Brunner et al., "Basic fibroblast growth factor expression in human bone marrow and peripheral blood cells," Blood, 81:631-638, 1993.
Burns et al., "Thymidine analogs are transferred from prelabeled donor to host cells in the central nervous system after transplantation: a word of caution," Stem Cells, 24:1121-1127, 2006.
Campagnoli et al., "Identification of Mesenchymal Stem/Progenitor Cells in Human FirstTrimester Fetal Blood, Liver, and Bone Marrow," Blood, 98(8):2396-2402 (2001).
Caplan et al., "Mesenchymal Stem Cells as Trophic Mediators," J. Cell Biochem. 98:1076-1084 (2006).
Chen et al. "Analysis of allogenicity of mesenchymal stem cells in engraftment and wound healing in mice," PLoS One., 4(9):e7119, 2009, doi: 10.1371/journal.pone.0007119.
Chen et al., "Neurorestorative therapy for stroke," Front Hum Neurosci., 8:382, 2014.
Cheng et al., "Mechanical strain tightly controls fibroblast growth factor 2 release from cultured human vascular smooth muscle cells," Circ Res., 80:28-36, 1997.
Clarke et al., "Contraction-induced cell wounding and release of fibroblast growth factor in heart," Circ Res., 76:927-934, 1995.
Conget et al., "Identification of a Discrete Population of Human Bone Marrow-Derived Mesenchymal Cells Exhibiting Properties of Uncommitted Progenitors" J. Hematother. Stem Cell Res., 10:749-758, (2001).
Coyne et al., "Marrow stromal cells transplanted to the adult brain are rejected by an inflammatory response and transfer donor labels to host neurons and glia," Stem Cells., 24:2483-2492, 2006.
D'Amore, PA, "Modes of FGF release in vivo and in vitro," Cancer Metastasis Rev., 9:227-238, 1990.
Dao et al., "Comparing the Angiogenic Potency of Naive Marrow Stromal Cells and Notch-Transfected Marrow Stromal Cells," J Translational Medicine, 11:81-91 (2013).
Del Amo, F. et al., "Cloning, Analysis and Chromosomal Localization of Notch-I, a Mouse Homolog of *Drosophilia* Notch," Genomics, 12:259-264 (1993).
Dezawa et al. "Sciatic Nerve Regeneration in Rats Induced by Transplantation of In Vitro Differentiated Bone-Marrow Stromal Cells," The European Journal of Neuroscience 14(11):1771-1776 (2001).
Dezawa, et al., "Specific Induction of Neuronal Cells From Bone Marrow Stromal Cells and Application for Autologous Transplantation," J Clin Invest 113(12):1701-1710 (2004).
Ehebauer et al., "Notch Signaling Pathway," Sci. STKE, 2006(364):cm7 (2006).
Erices et al., "Mesenchymal Progenitor Cells in Human Umbilical Cord Blood," Br. J Haematol., 109(1):235-242 (2000).
Fukuo et al., "Nitric oxide mediates cytotoxicity and basic fibroblast growth factor release in cultured vascular smooth muscle cells: a possible mechanism of neovascularization in atherosclerotic plaques," J Clin Invest., 95:669-676, 1995.
Gajdusek et al., "Injury-induced release of basic fibroblast growth factor from bovine aortic endothelium," J Cell Physiol., 139:570-579, 1989.
Galderisi et al., "Efficient 1-16 cultivation of neural stem cells with controlled delivery of FGF-2", Stem Cell Research, vol. 10, No. 1, pp. 85-94, Jan. 1, 2013, XP055513287, NL ISSN: 1873-5061, DOI: 10.1016/j.scr.2012.09.001.
GenBank Accession No. CAB40733 (Apr. 15, 2005).
Gonzalez et al., "Storage, metabolism, and processing of 125I-fibroblast growth factor-2 after intracerebral injection," Brain Res., 665:285-292, 1994.
Griffin et al., "Anti-donor immune responses elicited by allogeneic mesenchymal stem cells: what have we learned so far?" Immunol Cell Biol., 91:40-51, 2013.
Hartnett et al., "Release of bFGF, an endothelial cell survival factor, by osmotic shock," Invest Ophthalmol Vis Sci., 40:2945-2951, 1999.

Hou et al., "Induction of Umbilical Cord Blood Mesenchymal Stem Cells Into Neuron-Like Cells In Vitro," Int. J Hematol., 78(3):256-261 (2003).
Ikeda et al., "Bone marrow stromal cells that enhanced fibroblast growth factor-2 secretion by herpes simplex virus vector improve neurological outcome after transient focal cerebral ischemia in rats," Stroke, 36:2725-2730, 2005.
Isakova et al., "Preclinical evaluation of adult stem cell engraftment and toxicity in the CNS of rhesus macaques," Mol Ther., 3:1173-1184, 2006.
Jiang et al., "Pluripotency of Mesenchymal Stem Cells Derived From Adult Marrow," Nature 418:41-49 (2002).
Jiao et al., "A Mesenchymal Stem Cell Potency Assay," Methods Mol Biol., 677:221-231, 2011.
Joyce et al., "Mesenchymal stem cells for the treatment of neurodegenerative disease," Regen Med., 5:933-946, 2010.
Kaye et al., "Role of transiently altered sarcolemmal membrane permeability and basic fibroblast growth factor release in the hypertrophic response of adult rat ventricular myocytes to increased mechanical activity in vitro," J Clin Invest., 97:281-291, 1996.
Li et al., "Postischemic administration of basic fibroblast growth factor improves sensorimotor function and reduces infarct size following permanent focal cerebral ischemia in the rat," Exp Neurol., 177:531-537, 2002.
Liao et al., "Biological functions 1-16 of the low and high molecular weight protein isoforms of fibroblast growth factor-2 in cardiovascular development and disease", Developmental Dynamics, vol. 238, No. 2, pp. 249-264, Sep. 4, 2008, XP055513248, US, ISSN: 1058-8388, DOI: 10.1002/dvdy.21677.
Liekens et al., "Angiogenesis: regulators and clinical applications," Biochemical Pharmacology, 61:253-270, 2001.
Liew et al., "Therapeutic potential for mesenchymal stem cell transplantation in critical limb ischemia," Stem Cell Res Ther., 3:28, 2012.
Liu et al., "Mesenchymal stem cells prevent hypertrophic scar formation via inflammatory regulation when undergoing apoptosis," J Invest Dermatol., 134:2648-2657, 2014.
Madrigal et al., "A review of therapeutic effects of mesenchymal stem cell secretions and induction of secretory modification by different culture methodsm," J Transl Med., 12:260, 2014.
Marconi, Silvia et al., "Human Adipose-Derived Mesenchymal Stem Cells Systemically Injected Promote Peripheral Nerve Regeneration in the Mouse Model of Sciatic Crush," Tissue Engineering: Part A, vol. 18, Nos. 11 and 12, pp. 1264-1272, 2012.
McNeil et al., "Growth factors are released by mechanically wounded endothelial cells," J Cell Biol., 109:811-822, 1989.
Minguell et al., "Mesenchymal Stem Cells," Exp. Biol. Med., 226:507-520, (2001).
Mishra et al., "Cell-free derivatives from mesenchymal stem cells are effective in wound therapy," World J Stem Cells, 4: 35-43, 2012.
Mumm et al., "Notch Signaling: From the Outside in," Dev. Biol., 228(2):151-165 (2000).
Muthukrishnan et al., "Basic fibroblast growth factor is efficiently released from a cytolsolic storage site through plasma membrane disruptions of endothelial cells," J Cell Physiol., 148:1-16, 1991.
NCBI Reference Sequence No. NM_017167 (Apr. 29, 2013).
Parekkadan et al., "Mesenchymal Stem Cell-Derived Molecules Reverse Fulminant Hepatic Failure," PLoS ONE, 2: e941, 2007.
Pittenger et al., "Multilineage Potential of Adult Human Mesenchymal Stem Cells," Science 284(5411):143-147 (1999).
Prockop et al., "Marrow Stromal Cells as Stem Cells for Nonhematopoietic Tissues," Science 276(5309):71-74 (1997).
Quertainmont, Renaud et al., "Mesenchymal Stem Cell Graft Improves Recovery after Spinal Cord Injury in Adult Rats through Neurotrophic and Pro-Angiogenic Actions," Mesenchymal Stem Cells for Spinal Cord Injury, vol. 7, Iss. 6, pp. 1-15, Jun. 2012.
Richardson et al., "Cerebral perfusion in chronic stroke: implications for lesion-symptom mapping and functional MRI," Behav Neurol., 24:117-122, 2011.
Sanchez-Muroz, Isabel et al., "The Use of Adipose Mesenchymal Stem Cells and Human Umbilical Vascular Endothelial Cells on a Fibrin Matrix for Endothelialized Skin Substitute," Tissue Engineering: Part A, vol. 21, Nos. 1 and 2, pp. 214-223, 2015.

(56) References Cited

OTHER PUBLICATIONS

Schroeter et al., "Notch-1 Signalling Requires Ligand-Induced Proteolytic Release of Intracellular Domain," Nature, 393:382-386 (1998).
Spaggiari et al., "Mesenchymal stem cell-natural killer cell interactions: evidence that activated NK cells are capable of killing MSCs, whereas MSCs can inhibit IL-2-induced NK-cell proliferation," Blood, 107:1484-1490, 2006.
SwissProt P46531 (Nov. 1, 1995).
SwissProt QOI705 (Nov. 1, 1995).
Tate et al., "Human Mesenchymal Stromal Cells and Their Derivative, SB623 Cells, Rescue Neural Cells via Trophic Support Following In Vitro Ischemia," Cell Transplantation, vol. 19, pp. 973-984, 2010.
Tate et al., "SB623 Cells Promote 1-16 Angiogenesis—A Potential Mechanism of Action for Enhancing Neural Regeneration", Cell Transplantation, Sage, US, vol. 21, No. 4, p. 794, Jan. 1, 2012, XP009169862, ISSN: 0963-6897.
Van Roemeling et al., "Human Allogeneic Bone Marrow and Adipose Tissue Derived Mesenchymal Stromal Cells Induce CD8+ Cytotoxic T Cell Reactivity," J Stem Cell Res Ther., 3(Suppl 6):004, 2013.
Vu et al., "Meta-analysis of preclinical studies of mesenchymal stromal cells for ischemic stroke," Neurology, 82:1277-1286, 2014.
Wang et al., "Intranasally delivered bFGF enhances neurogenesis in adult rats following cerebral ischemia," Neurosci Lett., 446:30-35, 2008.
Watanabe et al., "Postischemic intraventricular administration of FGF-2 expressing adenoviral vectors improves neurologic outcome and reduces infarct volume after transient focal cerebral ischemia in rat,". J Cereb Blood Flow Metab., 24:1205-1213, 2004.
Weinmaster et al., "A Homolog of *Drosophila* Notch Expressed During Mammalian Development," Development 113:199-205 (1991).
Westrich et al., "Factors affecting residence time of mesenchymal stromal cells (MSC) injected into the myocardium," Cell Transplant., 19:937-848, 2010.
Witte et al., "Effects of irradiation on the release of growth factors from cultured bovine, porcine, and human endothelial cells," Cancer Res., 49:5066-5072, 1989.
Xiong et al., "Angiogenesis, neurogenesis and brain recovery of function following injury," Curr Opin Investig Drugs, 11:298-308, 2010.
Yu et al., "Basic fibroblast growth factor (FGF-2): the high molecular weight forms come of age," J. Cell Biochem, 100(5):1100-1108, (Apr. 1, 2007).

\* cited by examiner

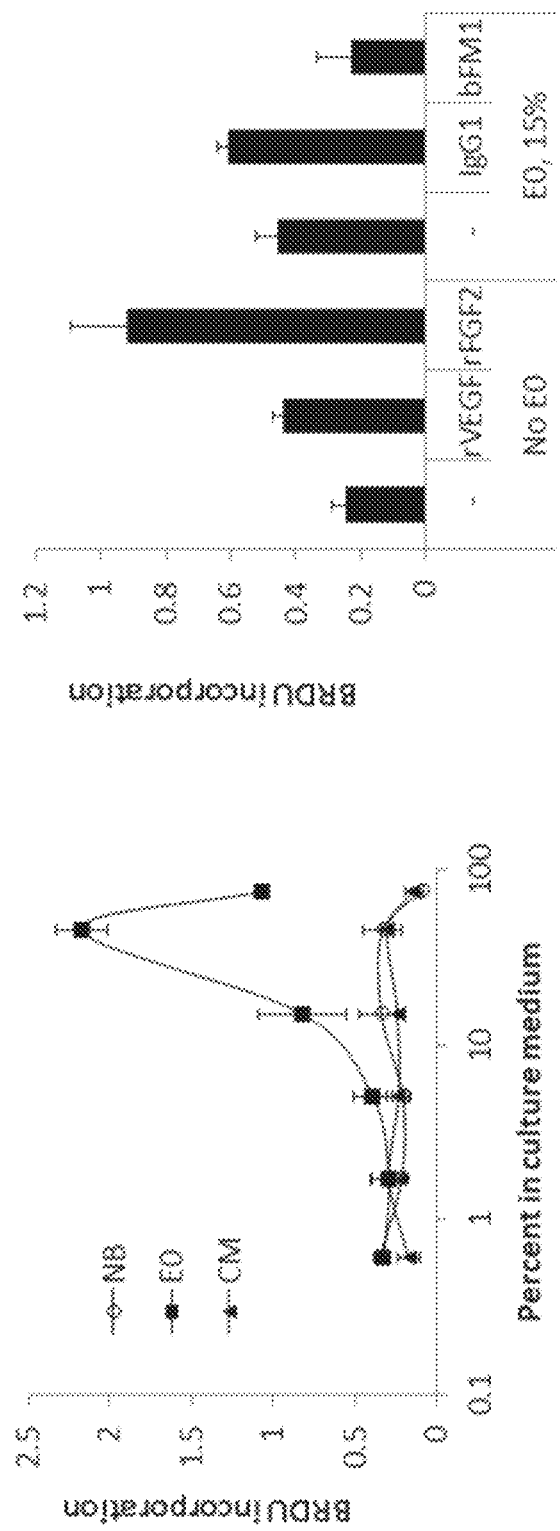

FIGURE 4A
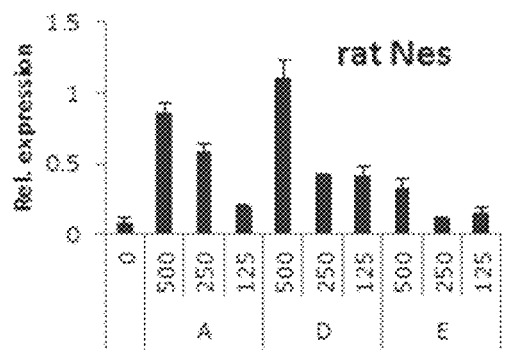
FIGURE 4D
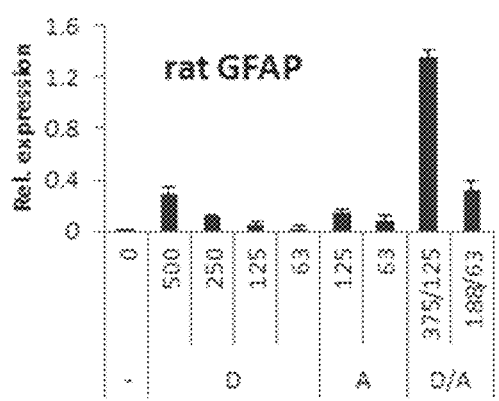
FIGURE 4B
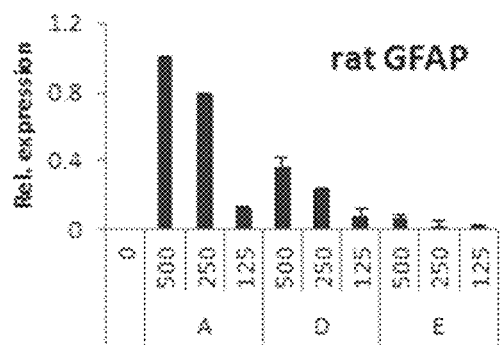
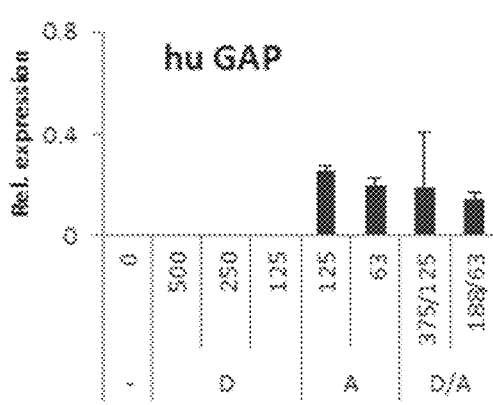
FIGURE 4E
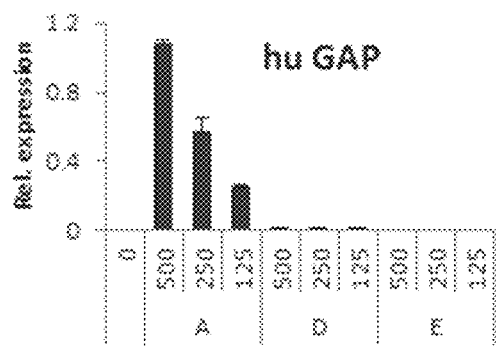
FIGURE 4C

FIGURE 6A
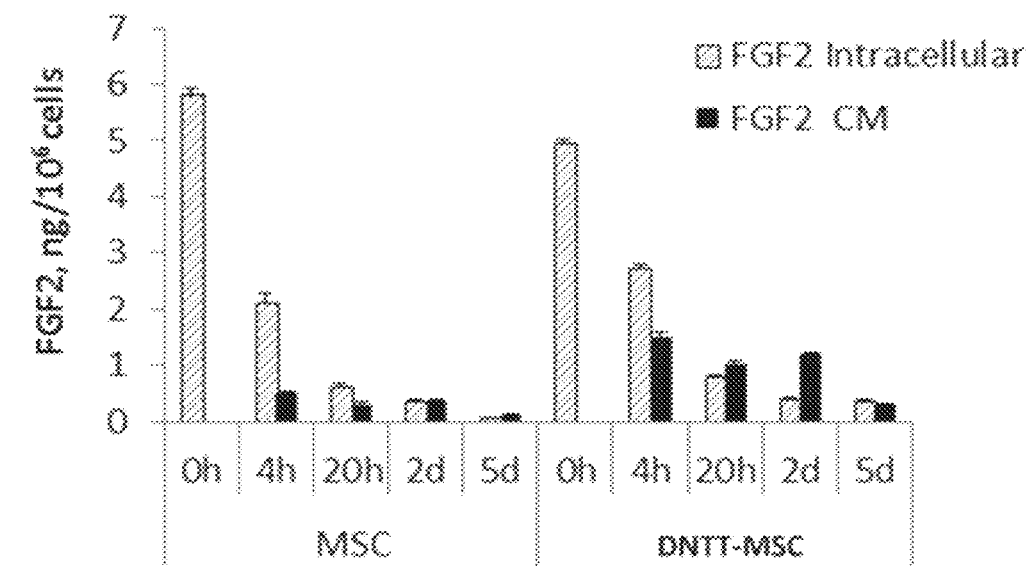
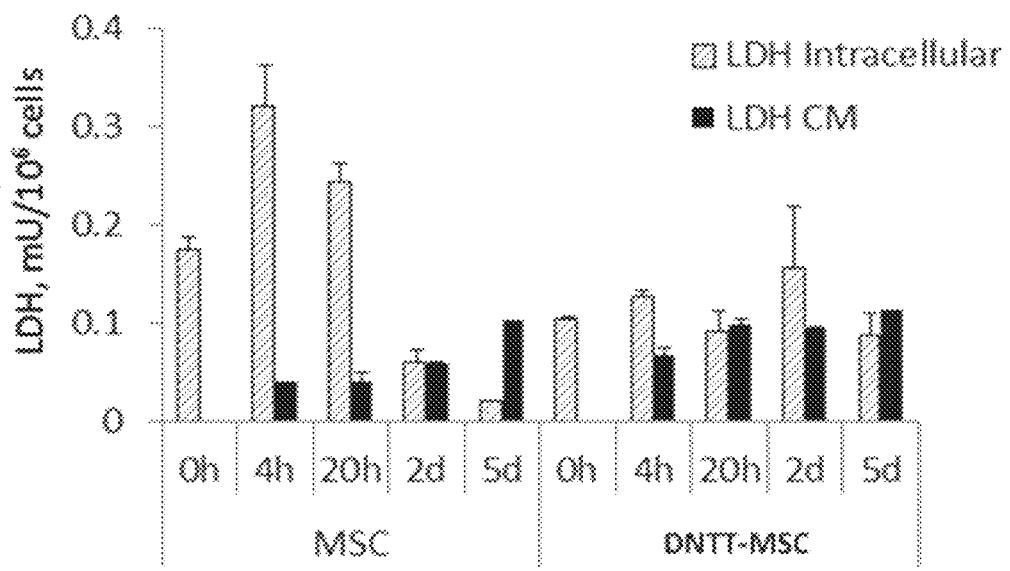
FIGURE 6B

METHODS AND COMPOSITIONS FOR STIMULATION OF CELL PROLIFERATION AND PROVISION OF BIOLOGICALLY ACTIVE MIXTURES OF FGF2 ISOFORMS

CROSS REFERENCE TO RELATED APPLICATIONS

This application is a continuation of U.S. patent application Ser. No. 15/710,528 filed Sep. 20, 2017, which is a continuation of International Patent Application No. PCT/US2016/025559 filed Apr. 1, 2016, which claims the benefit under 35 U.S.C. § 119(e), of U.S. Provisional Patent Application No. 62/178,190 filed Apr. 1, 2015 and U.S. Provisional Patent Application No. 62/204,776 filed Aug. 13, 2015; the disclosures of which are hereby incorporated by reference in their entireties for all purposes.

STATEMENT REGARDING FEDERAL SUPPORT

Not applicable.

FIELD

This disclosure is in the field of growth factors and their effects on the proliferation and development of cells, particularly neural cells and cells associated with the nervous system.

BACKGROUND

Mesenchymal Cell Implantation

Implantation of mesenchymal stromal cells (MSCs) and their derivatives is being developed as a treatment for various degenerative disorders of the central nervous system (CNS). The therapeutic effects resulting from MSC implantation into the CNS are thought to be due primarily to the secretion of soluble factors from living implanted cells, which provide tissue protective, regenerative, and immunomodulatory stimuli [1-3]. Paradoxically, however, the engraftment rate of MSCs in the CNS subsequent to implantation is low [4,5]; and therapeutic benefits have been observed to continue long after the grafted cells can no longer be detected. A variety of explanations have been proposed to account for the poor engraftment of implanted MSCs. Some investigators suggest the triggering of innate, and subsequent adaptive, immune responses to explain graft loss; however, others find similar rates of graft cell loss irrespective of HLA matching status [6,7]. Additional studies have provided evidence that allogeneic MSCs do not elicit a significant immune response after implantation (reviewed in [8]). It has also been reported that intracellularly labeled MSCs (either alive or dead), implanted into the adult brain, can transfer labels to surrounding and distant cells of the recipient, and the labels can become incorporated into cells of the recipient [9,10].

FGF-2

FGF2 (also known as basic fibroblast growth factor, or bFGF) is a major growth factor for stem cells, a potent inducer of angiogenesis, an essential wound healing mediator, and a major player in the development and regeneration of the nervous system (reviewed in [11]). Five FGF2 isoforms are translated from a unique FGF2 mRNA by alternative translation initiation: an 18 kD low molecular weight (LMW) isoform; and high molecular weight (HMW) isoforms comprising molecular weights of 22, 22.5, 24, and 34 kD. LMW FGF2 is mostly cytoplasmic and is secreted, while the HMW isoforms are predominantly nuclear, however any of the isoforms can be found in the nucleus, cytoplasm, or extracellular matrix under certain conditions. All isoforms lack a signal peptide to direct secretion through the endoplasmic reticulum-Golgi pathway. Early studies demonstrated that mechanically wounded monolayers of endothelial cells release high levels of FGF2 [12, 13]. Based on these studies and the lack of signal peptide for secretion, cell death or even sub-lethal injury have been described as a major mechanism for FGF2 release [14]. Accordingly, FGF2 has been nominated as a "wound hormone for rapidly initiating the cell growth required for routine maintenance of tissue integrity and/or repair after injury" [15].

While many reports document the expression of FGF2 mRNA by MSCs and demonstrate the presence of intracellular FGF2 protein [11, 12, 16], very few reports provide measurements of FGF2 secretion, because the concentration of secreted FGF2 is very low [17, 18]. Perhaps for this reason, FGF2 has not been considered to be a primary candidate for mediating the regenerative effects of implanted MSC on surrounding neural tissue.

DNTT-MSCs

DNTT-MSCs ("descendants of NICD transiently-transfected MSCs") are a population of cells that can be derived from human bone marrow MSCs by transient transfection of MSCs with a vector encoding the Notch intracellular domain (NICD); e.g., the human Notch1 intracellular domain (NICD1), followed by selection and subsequent expansion. This process produces a cell population that demonstrates superior angiogenic and neuropoietic (i.e., growth and differentiation of neural precursor cells) properties in vitro, compared to the parental MSCs [19-21]. The neuropoietic effects of DNTT-MSCs have been attributed to the increased expression, and correspondingly, increased secretion, of FGF1, FGF2, and BMPs [19, 22].

However, very low levels of FGF2 are secreted by MSCs or DNTT-MSCs. Tate et al. (2010) *Cell Transplantation* 19: 973-984. Accordingly, if FGF2 is responsible, in whole or in part, for the neuropoietic effects of MSCs and/or DNTT-MSCs, its source remains elusive.

SUMMARY

Mesenchymal cells (e.g., fibroblasts, MSCs and DNTT-MSCs) contain intracellular stores of FGF2; but very little of the intracellular FGF2 is secreted in culture. Rather, damage to, or death of, mesenchymal cells results in the release of their intracellular FGF2. The inventors have discovered that mesenchymal cells contain particularly large intracellular stores of FGF2, which, upon release, can exert neuropoietic and angiogenic effects on vicinal cells or tissue in a number of in vitro model systems. Moreover, mesenchymal cells contain a mixture of FGF2 isoforms, and this mixture of isoforms possesses greater biological activity than does a single isoform (i.e., recombinant FGF2).

Accordingly, the present disclosure provides, inter alia, the following embodiments.

1. A method for inducing proliferation of a neural precursor cell or an endothelial cell, the method comprising contacting the neural precursor cell or the endothelial cell with a preparation, obtained from mesenchymal cells, selected from the group consisting of a cell lysate, a soluble cell-free extract and an insoluble cell residue.

2. A method for inducing development of an astrocyte precursor cell to an astrocyte, the method comprising contacting the astrocyte precursor cell with a mixture of live mesenchymal cells and a cell lysate of mesenchymal cells.

3. A method for providing a mixture of FGF2 isoforms to a cell or tissue, the method comprising contacting the cell or tissue with a preparation, obtained from mesenchymal cells, selected from the group consisting of a cell lysate, a soluble cell-free extract, and an insoluble cell residue.

4. A method for delivering a mixture of FGF2 isoforms to a subject in need thereof, the method comprising introducing, into the subject, a preparation, obtained from mesenchymal cells, selected from the group consisting of a cell lysate, a soluble cell-free extract and an insoluble cell residue.

5. The method of embodiment 3, wherein the mixture comprises FGF2 isoforms that have molecular weights of 18, 22, 22.5 and 24 kD.

6. The method of embodiment 4, wherein the mixture comprises FGF2 isoforms that have molecular weights of 18, 22, 22.5 and 24 kD.

7. The method of embodiment 3, wherein the mixture has a greater biological activity that that of recombinant FGF2.

8. The method of embodiment 4, wherein the mixture has a greater biological activity that that of recombinant FGF2.

9. The method of embodiment 3, wherein the cell is a neural precursor cell.

10. The method of embodiment 3, wherein the cell is an endothelial cell.

11. The method of embodiment 4, wherein the subject has undergone an ischemic injury.

12. The method of embodiment 11, wherein the ischemic injury is a stroke.

13. The method of embodiment 3, wherein the tissue is necrotic.

14. The method of embodiment 13, wherein necrosis results from infarction or traumatic injury.

15. The method of embodiment 1, wherein the mesenchymal cells are selected from the group consisting of fibroblasts, mesenchymal stem cells (MSCs) and DNTT-MSCs.

16. The method of embodiment 2, wherein the mesenchymal cells are selected from the group consisting of fibroblasts, mesenchymal stem cells (MSCs) and DNTT-MSCs.

17. The method of embodiment 3, wherein the mesenchymal cells are selected from the group consisting of fibroblasts, mesenchymal stem cells (MSCs) and DNTT-MSCs.

18. The method of embodiment 4, wherein the mesenchymal cells are selected from the group consisting of fibroblasts, mesenchymal stem cells (MSCs) and DNTT-MSCs.

19. A method for delivering a biologically active mixture of FGF2 isoforms to a tissue, the method comprising:
contacting the tissue with mesenchymal cells;
wherein said contact results in lysis or rupture of the mesenchymal cells.

20. The method of embodiment 19 wherein the FGF2 isoforms have molecular weights of 18, 22, 22.5 and 24 kD.

21. The method of embodiment 19, wherein the mixture has a greater biological activity that that of recombinant FGF2.

22. The method of embodiment 19, wherein the tissue comprises one or more neural precursor cells.

23. The method of embodiment 19, wherein the tissue comprises one or more endothelial cells.

24. The method of embodiment 19, wherein the tissue is present in a subject that has undergone an ischemic injury.

25. The method of embodiment 24, wherein the ischemic injury is a stroke.

26. The method of embodiment 19, wherein the tissue is necrotic.

27. The method of embodiment 26, wherein necrosis results from infarction or traumatic injury.

28. The method of embodiment 19, wherein the mesenchymal cells are selected from the group consisting of fibroblasts, mesenchymal stem cells (MSCs) and DNTT-MSCs.

29. A cell-free extract of mesenchymal cells for use in a method of stimulating the proliferation of neural precursor cells or endothelial cells, wherein the mesenchymal cells are selected from the group consisting of fibroblasts, MSCs and DNTT-MSCs.

30. A cell lysate of mesenchymal cells for use in a method of stimulating the proliferation of neural precursor cells or endothelial cells, wherein the mesenchymal cells are selected from the group consisting of fibroblasts, MSCs and DNTT-MSCs.

31. An insoluble cell residue of mesenchymal cells for use in a method of stimulating the proliferation of neural precursor cells or endothelial cells, wherein the mesenchymal cells are selected from the group consisting of fibroblasts, MSCs and DNTT-MSCs.

32. A combination for use in a method of stimulating the proliferation of neural precursor cells or endothelial cells, wherein the combination comprises:
(a) fibroblast growth factor-2 (FGF2), and
(b) conditioned medium from a mesenchymal cell, wherein the mesenchymal cell is selected from the group consisting of fibroblasts, MSCs and DNTT_MSCs.

33. The combination of embodiment 32, wherein the FGF 2 is recombinant.

34. The combination of embodiment 32, wherein the FGF 2 is the 18 kd isoform.

35. A combination for use in a method of inducing development of an astrocyte precursor cell to an astrocyte, wherein the combination comprises:
(a) live mesenchymal cells, wherein the mesenchymal cells are selected from the group consisting of fibroblasts, MSCs and DNTT-MSCs; and
(b) a preparation, obtained from mesenchymal cells, wherein the preparation is selected from the group consisting of a cell lysate and a soluble cell-free extract.

36. The combination of embodiment 35, wherein the ratio of lysate cell equivalents to live cells is 3:1.

37. A preparation, obtained from mesenchymal cells, for use in a method of providing a mixture of FGF2 isoforms to a cell, tissue, or subject in need thereof;
wherein the preparation is selected from the group consisting of a cell lysate, a soluble cell-free extract and an insoluble cell residue;
further wherein the mesenchymal cells are selected from the group consisting of fibroblasts, MSCs and DNTT-MSCs.

38. The preparation of embodiment 37, wherein the mixture of FGF2 isoforms contains FGF2 isoforms having molecular weights of 18, 22, 22.5 and 24 kD.

39. The preparation of embodiment 37, wherein the mixture of FGF2 isoforms has greater biological activity than that of recombinant FGF2.

40. The preparation of embodiment 37, wherein the cell is a neural precursor cell or an endothelial cell.

41. The preparation of embodiment 37, wherein the tissue comprises one or more of an neural precursor cell and/or an endothelial cell.

42. The preparation of embodiment 37, wherein the tissue or subject has undergone an ischemic injury.

43. The preparation of embodiment 42, wherein the ischemic injury is a stroke.

44. The preparation of embodiment 37, wherein the tissue is necrotic.

45. The preparation of embodiment 44, wherein necrosis results from infarction or traumatic injury.

46. A method for stimulating the proliferation of neural precursor cells or endothelial cells; the method comprising contacting the neural precursor cells or endothelial cells with the combination of embodiment 32.

BRIEF DESCRIPTION OF THE DRAWINGS

FIG. 1A shows FGF2 levels in freeze-thaw cell-free extracts (E0 extracts) from MSCs (left bar) and DNTT-MSCs (right bar), measured by FGF2 ELISA.

FIG. 1B shows FGF2 levels in conditioned medium (CM) from MSCs (left bar) and DNTT-MSCs (right bar), measured by HS-FGF2 ELISA.

FIG. 1C shows LDH levels in cell-free E0 extracts (left bar in each pair) and cell-free E1 extracts (right bar in each pair) in MSCs (left pair of bars) and DNTT-MSCs (right pair of bars). Bars represent the average across 7 cell lots. Error bars represent standard deviation.

FIG. 2A shows levels of BRDU incorporation by neural cells exposed to increasing concentrations of cell-free E0 extract (filled squares) or conditioned medium (open circles) from MSCs.

FIG. 2B shows levels of BRDU incorporation by neural cells exposed to 0, 5, or 15% cell-free E0 extract (equivalent to 0, 0.07 or 0.2 ng/ml FGF2, respectively) in the presence of anti-FGF2 antibody (bFM1) or control immunoglobulin (IgG1).

FIGS. 3A and 3B show measurements of endothelial cell proliferation assayed by BRDU incorporation.

FIG. 3A shows levels of BRDU incorporation by HUVEC exposed to increasing concentrations of cell-free E0 extract (filled squares) or conditioned medium (filled triangles) from MSCs. NeuroBasal (NB) medium (open circles) was used as a negative control.

FIG. 3B shows levels of BRDU incorporation by control HUVEC (left-most bar), HUVEC exposed to 10 ng/ml recombinant vascular endothelial growth factor (rVEGF, second bar from left), and HUVEC exposed to 1 ng/ml recombinant fibroblast growth factor-2 (rFGF2, third bar from left). Also shown are levels of BRDU incorporation by HUVEC exposed to 15% cell-free E0 extract from DNTT-MSCs (third bar from right), HUVEC exposed to 15% cell-free E0 extract from DNTT-MSCs in the presence of a control immunoglobulin (IgG1, second bar from right) or HUVEC exposed to 15% cell-free E0 extract from DNTT-MSCs in the presence of an anti-FGF2 antibody (bFM1, right-most bar).

FIGS. 4A-4E show expression levels of neuronal and glial markers induced by live cells, dead cell suspensions (i.e., cell lysates) and cell-free extracts from DNTT-MSCs.

FIG. 4A shows levels of rat nestin expressed in rat cortical cell cultures containing live DNTT-MSCs (A), dead (freeze-thawed) DNTT-MSCs (i.e., DNTT-MSC cell lysates) (D), or cell-free extracts of DNTT-MSCs (E). The number of DNTT-MSCs or cell equivalents used in each assay were 125, 250 or 500, as indicated.

FIG. 4B shows levels of rat GFAP expressed in rat cortical cell cultures (the same cultures that were assayed in FIG. 4A) containing live DNTT-MSCs (A), dead (freeze-thawed) DNTT-MSCs (i.e., DNTT-MSC cell lysates) (D), or cell-free extracts of DNTT-MSCs (E). The number of DNTT-MSCs or cell equivalents used in each assay were 125, 250 or 500, as indicated.

FIG. 4C shows levels of human GAP expressed in rat cortical cell cultures (the same cultures that were assayed in FIG. 4A) containing live DNTT-MSCs (A), dead (freeze-thawed) DNTT-MSCs (i.e., DNTT-MSC cell lysates) (D), or cell-free extracts of DNTT-MSCs (E). The number of DNTT-MSCs or cell equivalents used in each assay were 125, 250 or 500, as indicated.

FIG. 4D shows levels of rat GFAP expressed in rat cortical cell cultures containing live DNTT-MSCs (A), dead DNTT-MSCs (i.e., DNTT-MSC cell lysates) (D), or mixtures of live and dead DNTT-MSCs (D/A). Numbers of DNTT-MSCs or cell equivalents are shown along the X axis.

FIG. 4E shows levels of human GAP expressed in rat cortical cell cultures (the same cultures that were assayed in FIG. 4D) containing live DNTT-MSCs (A), dead DNTT-MSCs (i.e., DNTT-MSC cell lysates) (D), or mixtures of live and dead DNTT-MSCs (D/A). Numbers of DNTT-MSCs or cell equivalents are shown along the X axis.

FIG. 5A shows percentage of total intracellular LDH released into culture medium from target cells (leftmost, shaded bar in each pair) and percentage of total intracellular FGF2 released into culture medium from the same preparation of target cells (rightmost, solid bar in each pair) following co-culture of target cells with PBMCs for 18 hours. Target cells were MSCs (M) and DNTT-MSCs (S). PBMCs were co-cultured with target cells at PBMC:target cell ratios of 30:1 (30×P) and 10:1 (10×P).

FIG. 5B shows FGF2 concentrations in cultures of target cells, lysed target cells and co-cultures. Intact target cells were MSCs (M) or DNTT-MSCs (S). Target cells were lysed in 1% Triton ("M lysed" and "S lysed"). Co-cultures contained either a 10-fold (10×P) or a 30-fold (30×P) excess of PBMCs to target cells. FGF2 concentration was also measured in a sample of PBMCs containing the same number of PBMC as was present in the 30×P co-culture samples (30×PBMC).

FIGS. 6A and 6B show levels of intracellular and extracellular FGF2 and LDH in hypoxic cultures of MSCs and DNTT-MSCs.

FIG. 6A shows concentrations of intracellular FGF2 ("FGF2 Intracellular," crosshatched bars) and extracellular FGF2 ("FGF2 CM," solid bars) in cultures of MSCs and DNTT-MSCs at initiation of culture under hypoxic conditions ("0 h"), and various times thereafter (4 hours, 20 hours, 2 days and 5 days).

FIG. 6B shows concentrations of intracellular lactate dehydrogenase ("LDH Intracellular," crosshatched bars) and extracellular lactate dehydrogenase ("LDH CM," solid bars) in cultures of MSCs and DNTT-MSCs at initiation of culture under hypoxic conditions ("0 h"), and various times thereafter (4 hours, 20 hours, 2 days and 5 days).

FIG. 7A shows levels of BRDU incorporation by neural cells exposed to increasing concentrations of recombinant FGF2, (rFGF2, triangles) and by neural cells exposed to increasing concentrations of recombinant FGF2 in the presence of 75% conditioned medium from DNTT-MSCs (circles). Also shown is a hypothetical curve that was calculated based on the assumption that the response to rFGF2 and CM is additive (squares).

FIG. 7B shows levels of BRDU incorporation by neural cells exposed to increasing concentrations of rFGF2 (0-10 ng/ml); increasing concentrations of rFGF2 (0-10 ng/ml) together with 75% conditioned medium from DNTT-MSCs (DNTT-MSC-CM, 75%) or increasing concentrations of a DNTT-MSCs freeze/thaw extract (DNTT-MSC-E0).

FIG. 10A shows levels of FGF2 in fractions from HFFs and MSCs (D94M). The fractions assayed are cell lysates ("Dead"), cell-free extracts ("E0") and cell residues ("Pellet").

FIG. 10B shows neural cell proliferation (as measured by BrdU incorporation) in neural cells exposed to increasing concentrations of cell lysate ("Dead susp"), cell-free E0 extracts ("E0"), and resuspended cell residue ("Pellet susp") from HFFs and MSCs (D94M). "No add" indicates no addition.

FIG. 10C shows the effect of noggin (50 ng/ml) (rightmost of each pair of bars) on neural precursor cell proliferation induced by MSC cell lysates (D94M-Dead), HFF cell lysates (HFF-Dead susp) and MSC cell residue (D94M-pellet). "No add" indicates no addition.

DETAILED DESCRIPTION

Figures 1A, 1B:
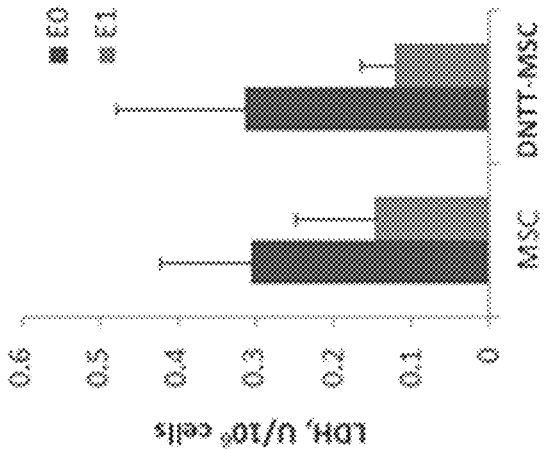
FIGS. 1A-1C show levels of FGF2 and LDH in extracts or conditioned medium obtained from MSCs and DNTT-MSCs. All values were obtained from one million cells.

Practice of the present disclosure employs, unless otherwise indicated, standard methods and conventional techniques in the fields of cell biology, toxicology, molecular biology, biochemistry, cell culture, immunology, oncology, recombinant DNA and related fields as are within the skill of the art. Such techniques are described in the literature and thereby available to those of skill in the art. See, for example, Alberts, B. et al., "Molecular Biology of the Cell," $5^{th}$ edition, Garland Science, New York, N.Y., 2008; Voet, D. et al. "Fundamentals of Biochemistry: Life at the Molecular Level," $3^{rd}$ edition, John Wiley & Sons, Hoboken, N.J., 2008; Sambrook, J. et al., "Molecular Cloning: A Laboratory Manual," $3^{rd}$ edition, Cold Spring Harbor Laboratory Press, 2001; Ausubel, F. et al., "Current Protocols in Molecular Biology," John Wiley & Sons, New York, 1987 and periodic updates; Freshney, R. I., "Culture of Animal Cells: A Manual of Basic Technique," $4^{th}$ edition, John Wiley & Sons, Somerset, N J, 2000; and the series "Methods in Enzymology," Academic Press, San Diego, Calif.

For the purposes of the present disclosure, "angiogenesis" refers to the formation of new vasculature (e.g., blood vessels; e.g., veins, arteries, venules, arterioles, capillaries). Angiogenesis can occur by sprouting of new vessels from an existing vessel, and/or by in situ coalescence of endothelial cells to form new blood vessels. Angiogenesis also includes the attendant processes of matrix remodeling and cell recruitment (e.g., recruitment of smooth muscle cells, monocytes and/or pericytes). Angiogenesis further includes proliferation and/or migration of endothelial cells.

"Neuropoiesis" refers to the growth and/or differentiation of neural precursor cells (NPCs) into neurons and/or glial cells (e.g., astrocytes, oligodendrocytes). Examples of neuropoietic processes include, but are not limited to, NPC proliferation, neurogenesis (e.g., formation of new neurons) and gliogenesis (e.g., formation of astrocytes and/or oligodendrocytes). Other processes related to neuronal development include, for example, neurite outgrowth, outgrowth of axon(s), and outgrowth of dendrite(s).

"Mesenchymal cells" refer to cells of mesenchymal tissue (e.g., chondroblasts, chondrocytes, osteoblasts, osteocytes, adipocytes) and their precursors and include, for example, fibroblasts (e.g., human foreskin fibroblasts), MSCs (as defined herein) and cells derived from MSCs such as, for example, DNTT-MSCs, as defined herein.

"MSCs" ("mesenchymal stem cells") refer to adherent, non-hematopoietic pluripotent cells obtained from bone marrow. These cells are variously known as mesenchymal stem cells, mesenchymal stromal cells, marrow adherent stromal cells, marrow adherent stem cells and bone marrow stromal cells. MSCs can also be obtained from, e.g., umbilical cord blood, adipose tissue, dental pulp, Wharton's jelly, and various types of connective tissue.

The terms "DNTT-MSCs" ("descendants of NICD transiently-transfected MSCs") and "SB623 cells" refer to populations of cells obtained following transient expression of an exogenous Notch intracellular domain (NICD) in MSCs. For example, a population of DNTT-MSCs can be obtained by transient transfection of MSCs with a vector comprising sequences encoding a NICD (e.g., from the human Notch 1 protein) but not encoding full-length Notch protein, followed by selection (e.g., with G418). The selected cells are further cultured in a standard culture medium, optionally supplemented with a serum, in the absence of any added growth factors or differentiation factors (other than those which may be present in the serum, if serum is present in the culture medium).

"Conditioned medium" (CM) refers to cell culture medium in which cells have been incubated and subsequently removed after the incubation. Removal can include either removal of the cells from the medium, or removal of the medium from the cells. During incubation in medium, cell growth may or may not occur, depending upon the composition of the medium. For example, cells remain alive, but do not grow, in serum-free medium. The amount of time in which cells are incubated in medium prior to removal is indicated elsewhere in the specification. Conditioned medium can contain molecules synthesized and/or secreted by the cells incubated therein, and can also optionally be depleted of components that were present in the medium prior to the incubation of the cells therein.

For the purposes of the present disclosure, the terms "dead cells" and "cell lysate" are used to refer to a composition resulting from disruption of the integrity of the membrane of a cell, such that intracellular contents no longer remain inside an intact cell membrane. Disruption of said cell membrane can occur by any method known in the art, i.e., mechanically (e.g., by freeze-thaw, ultrasound, blending, shearing, homogenizing, etc.), thermally, chemically, biochemically, osmotically, immunologically, cytotoxically, and by evaporation, etc. Thus a cell lysate is composed of various insoluble cell structures and soluble cellular materials. Accordingly, the composition of a cell lysate can be further classified into two categories: an "insoluble fraction" and a "soluble fraction." The soluble and insoluble components can be separated, e.g., by centrifugation or filtration. The insoluble component is pelleted by centrifugation and/or is retained by a filter; while the soluble component remains in the supernatant after centrifugation and/or passes through a filter. The insoluble component can also be referred to as a "pellet" fraction or as "cell residue." Similarly, the soluble component can also be referred to as a "supernatant" fraction or as a "cell-free extract."

The terms "implantation" and "transplantation" are used to denote the introduction of exogenous cells into a subject. Exogenous cells can be autologous (i.e. obtained from the subject) or allogeneic (i.e., obtained from an individual other than the subject).

Mesenchymal Stem Cells (MSCs)

The present disclosure provides, inter alia, methods for providing biologically active FGF2 by implanting mesenchymal cells (e.g., fibroblasts, MSCs or DNTT-MSCs) to a site of CNS injury in a subject. MSCs are obtained by selecting (e.g., by growth in culture) adherent cells (i.e., cells that adhere to tissue culture plastic) from bone marrow. To obtain MSC populations having a sufficient number of cells for use in therapy, populations of adherent cells are expanded in culture after selecting for adherence. Expansion in culture also enriches for MSCs, since contaminating cells (such as monocytes) do not proliferate under the culture conditions.

Exemplary disclosures of MSCs are provided in U.S. patent application publication No. 2003/0003090; Prockop (1997) Science 276:71-74 and Jiang (2002) Nature 418:41-49. Methods for the isolation and purification of MSCs can be found, for example, in U.S. Pat. No. 5,486,359; Pittenger et al. (1999) Science 284:143-147 and Dezawa et al. (2001) Eur. J. Neurosci. 14:1771-1776. Human MSCs are commercially available (e.g., BioWhittaker, Walkersville, Md.) or can be obtained from donors by, e.g., bone marrow aspiration, followed by culture and selection for adherent bone marrow cells. See, e.g., WO 2005/100552.

MSCs can also be isolated from umbilical cord blood. See, for example, Campagnoli et al. (2001) Blood 98:2396-2402; Erices et al. (2000) Br. J. Haematol. 109:235-242 and Hou et al. (2003) Int. J. Hematol. 78:256-261. Additional sources of MSCs include, for example, adipose tissue, dental pulp and Wharton's jelly.

Notch Intracellular Domain

The Notch protein (e.g., Notch 1) is a transmembrane receptor, found in all metazoans, that influences cell differentiation through intracellular signaling. Contact of the Notch extracellular domain (e.g., the extracellular domain of the Notch 1 protein) with a Notch ligand (e.g., Delta, Serrate, Jagged) results in two proteolytic cleavages of the Notch protein, the second of which is catalyzed by a γ-secretase and releases the Notch intracellular domain (NICD) into the cytoplasm. In the mouse Notch protein, this cleavage occurs between amino acids gly1743 and val1744. The NICD translocates to the nucleus, where it acts as a transcription factor, recruiting additional transcriptional regulatory proteins (e.g., MAM, histone acetylases) to relieve transcriptional repression of various target genes (e.g., Hes 1).

Additional details and information regarding Notch signaling are found, for example in Artavanis-Tsakonas et al. (1995) Science 268:225-232; Mumm and Kopan (2000) Develop. Biol. 228:151-165 and Ehebauer et al. (2006) Sci. STKE 2006 (364), cm7. [DOI: 10.1126/stke.3642006cm7].

Cell Culture and Transfection

Standard methods for cell culture are known in the art. See, for example, R. I. Freshney "Culture of Animal Cells: A Manual of Basic Technique," Fifth Edition, Wiley, New York, 2005.

Methods for introduction of exogenous DNA into cells (i.e., transfection), and selection of transfected cells, are also well-known in the art. See, for example, Sambrook et al. "Molecular Cloning: A Laboratory Manual," Third Edition, Cold Spring Harbor Laboratory Press, 2001; Ausubel et al., "Current Protocols in Molecular Biology," John Wiley & Sons, New York, 1987 and periodic updates.

DNTT-MSCs

DNTT-MSCs are obtained from marrow adherent stromal cells, also known as mesenchymal stem cells (MSCs), by transiently expressing the intracellular domain of the Notch protein in the MSCs. Transient expression of the Notch intracellular domain (e.g., the NICD from the human Notch 1 protein)) in a MSC is sufficient to convert a population of MSCs to a population of DNTT-MSCs; additional treatment with growth and/or differentiation factors is not required. Thus, a population of MSCs can be converted to a population of DNTT-MSCs by transient transfection of MSCs with a vector comprising sequences encoding a NICD (but not encoding full-length Notch protein), followed by selection for cells comprising the vector and further culture of the selected cells in serum-containing medium, in the absence of exposure to additional growth and/or differentiation factors.

In one embodiment for the preparation of DNTT-MSCs, a culture of MSCs is contacted with a polynucleotide comprising sequences encoding a Notch intracellular domain (NICD); e.g., by transfection; followed by enrichment of transfected cells by drug selection and further culture. See, for example, U.S. Pat. No. 7,682,825 (Mar. 23, 2010); U.S. Patent Application Publication No. 2010/0266554 (Oct. 21, 2010); and WO 2009/023251 (Feb. 19, 2009); all of which disclosures are incorporated by reference, in their entireties, for the purposes of describing isolation of mesenchymal stem cells and conversion of mesenchymal stem cells to DNTT-MSCs (denoted "neural precursor cells" and "neural regenerating cells" in those documents).

In these methods, any polynucleotide encoding a Notch intracellular domain (e.g., vector) can be used, and any method for the selection and enrichment of transfected cells can be used. For example, in certain embodiments, MSCs are transfected with a vector containing sequences encoding a Notch intracellular domain (e.g., the human Notch 1 intracellular domain) and also containing sequences encoding a selection marker (e.g., drug resistance; e.g., resistance to G418). In additional embodiments, two vectors, one containing sequences encoding a Notch intracellular domain and the other containing sequences encoding a drug resistance marker, are used for transfection of MSCs. In these embodiments, selection is achieved, after transfection of a cell culture with the vector or vectors, by adding a selective agent (e.g., G418) to the cell culture in an amount sufficient to kill cells that do not comprise the vector but spare cells that do. Absence of selection entails removal of said selective agent or reduction of its concentration to a level that does not kill cells that do not comprise the vector. Following selection (e.g., for seven days) the selective agent is removed and the cells are further cultured (e.g., for two passages) in serum-containing culture medium.

It is also possible, depending on the nature of the selection marker and/or the concentration of the selective agent used, that not every cell that lacks a vector encoding a selection marker will be killed during the selection process. For example, a selective agent may inhibit growth of a cell not comprising the selection marker and, after removal of the selective agent, that cell may recover and resume growth.

Preparation of DNTT-MSCs thus involves transient expression of an exogenous Notch intracellular domain in a MSC. To this end, MSCs can be transfected with a vector comprising sequences encoding a Notch intracellular domain (e.g., the human Notch 1 intracellular domain) wherein said sequences do not encode a full-length Notch protein. All such sequences are well known and readily available to those of skill in the art. For example, Del Amo et al. (1993) *Genomics* 15:259-264 present the complete amino acid sequences of the mouse Notch protein; while Mumm and Kopan (2000) *Devel. Biol.* 228:151-165 provide the amino acid sequence, from mouse Notch protein, surrounding the so-called S3 cleavage site which releases the intracellular domain. Taken together, these references provide the skilled artisan with each and every peptide containing a Notch intracellular domain that is not the full-length Notch protein; thereby also providing the skilled artisan with every polynucleotide comprising sequences encoding a Notch intracellular domain that does not encode a full-length Notch protein. The foregoing documents (Del Amo and Mumm) are incorporated by reference in their entireties for the purpose of disclosing the amino acid sequence of the full-length Notch protein and the amino acid sequence of the Notch intracellular domain, respectively.

Similar information is available for Notch proteins and nucleic acids from additional species, including rat, *Xenopus, Drosophila* and human. See, for example, Weinmaster et al. (1991) *Development* 113:199-205; Schroeter et al. (1998) *Nature* 393:382-386; NCBI Reference Sequence No. NM_017167 (and references cited therein); SwissProt P46531 (and references cited therein); SwissProt Q01705 (and references cited therein); and GenBank CAB40733 (and references cited therein). The foregoing references are incorporated by reference in their entireties for the purpose of disclosing the amino acid sequence of the full-length Notch protein and the amino acid sequence of the Notch intracellular domain in a number of different species.

In additional embodiments, DNTT-MSCs are prepared by introducing, into MSCs, a nucleic acid comprising sequences encoding a Notch intracellular domain such that the MSCs do not express exogenous Notch extracellular domain. Such can be accomplished, for example, by transfecting MSCs with a vector comprising sequences encoding a Notch intracellular domain wherein said sequences do not encode a full-length Notch protein.

Additional details on the preparation of DNTT-MSCs, and methods for making cells with properties similar to those of DNTT-MSCs which can be used in the methods disclosed herein, are found in U.S. Pat. No. 7,682,825; and U.S. Patent Application Publication Nos. 2010/0266554 (Oct. 21, 2010) and 2011/0229442 (Sep. 22, 2011); the disclosures of which are incorporated by reference herein for the purposes of providing additional details on, and alternative methods for the preparation of, DNTT-MSCs, and for providing methods for making cells with properties similar to those of DNTT-MSCs. See also Dezawa et al. (2004) *J. Clin. Invest.* 113:1701-1710.

FGF2 Content of Mesenchymal Cells

Levels of FGF2 in extracts of MSCs and DNTT-MSCs are much higher than in conditioned media from these cells, indicating the existence of a large intracellular depot of biologically active FGF2 in MSCs and DNTT-MSCs, most of which is not secreted. Extracts obtained from mechanically-ruptured MSCs and DNTT-MSCs induced concentration-dependent proliferation of cortical neural progenitor cells and of umbilical vein endothelial cells; and the proliferation induced by MSC and DNTT-MSCs extracts was inhibited by an anti-FGF2 neutralizing antibody.

The quantity of FGF2 released from either MSCs or DNTT-MSCs by secretion versus mechanical cell injury was measured and compared. It is disclosed herein that contents released by mechanical cell injury were highly active in stimulating the proliferation of both neural precursor cells and endothelial cells. Furthermore, the mitogenic activity of these intracellular contents was shown to be due to release of intracellular FGF2. Models of alternative, non-mechanical cell injury that could lead to MSC death post intracerebral implantation demonstrated that substantial amounts of FGF2 are also released in these models, and that FGF2 release is correlated with death of MSCs or DNTT-MSCs. Finally it has been observed that co-cultures of mechanically injured and live mesenchymal cells work synergistically to influence the differentiation of neural progenitors.

Thus, the present disclosure shows that MSCs and DNTT-MSCs contain large intracellular stores of biologically active FGF2 that can be released following various types of cell injury, such as, for example, mechanical injury, cell-mediated cytotoxicity and hypoxia; upon which the released FGF 2 is able to stimulate cell proliferation, neuropoiesis, and angiogenesis. Accordingly, methods for, inter alia, stimulating proliferation and differentiation of neural precursor cells, and for stimulating proliferation of endothelial cells, by provision of dead mesenchymal cells (e.g., fibroblasts, MSCs and/or DNTT-MSCs), or by provision of soluble and/or insoluble intracellular extracts of mesenchymal cells (e.g., fibroblasts, MSCs and/or DNTT-MSCs), are provided. Dead mesenchymal cells (i.e. cell lysates), soluble cell-free extracts of mesenchymal cells, and insoluble cell residues of mesenchymal cells, for stimulating proliferation of neural and endothelial cells, are also provided.

In additional embodiments, methods and compositions for providing biologically active FGF2 (e.g., a mixture of two or more FGF2 isoforms) to a cell, tissue or subject are provided; wherein the methods comprise contacting the cell, tissue or subject with a soluble cell-free extract or an insoluble cell residue from a mesenchymal cell (e.g., fibroblasts, MSCs and/or DNTT-MSCs); or by contacting the cell, tissue or subject with dead mesenchymal cells (e.g., dead fibroblasts, dead MSCs and/or dead DNTT-MSCs).

In additional embodiments, mixtures of live mesenchymal cells (e.g., fibroblasts, MSCs and/or DNTT-MSCs) and cell-free extracts of mesenchymal cells (e.g., fibroblasts, MSCs and/or DNTT-MSCs) can be used to induce differentiation of an astrocyte precursor to an astrocyte. In further embodiments, compositions comprising mixtures of live mesenchymal cells (e.g., fibroblasts, MSCs and/or DNTT-MSCs) and cell-free extracts of mesenchymal cells are provided.

In additional embodiments, mixtures of live and dead mesenchymal cells (e.g., fibroblasts, MSCs and/or DNTT-MSCs) can be used to stimulate astrocyte development. Accordingly, mixtures of live and dead mesenchymal cells are also provided.

In further embodiments, mixtures of FGF2 (e.g., recombinant FGF2) and conditioned medium from a mesenchymal cell can be used to stimulate proliferation of neural precursor cells and/or endothelial cells. Accordingly mixtures of FGF2 (e.g., recombinant FGF2) and conditioned medium from a mesenchymal cell are also provided.

The compositions disclosed herein can be used for treatment of ischemic damage (e.g., stroke) and for treatment of necrosis. Necrosis can be caused by, inter alia, infarction (e.g., ischemia as occurs, for example, after a stroke) or injury (e.g., traumatic brain injury). Thus, necrotic tissue and disorders characterized by the presence of necrotic tissue can be treated with the compositions disclosed herein. In certain embodiments, a composition as disclosed herein is implanted (e.g., by injection) into viable tissue abutting the necrotic tissue. Thus, in the case of an infarct, the composition is implanted into peri-infarct tissue.

Formulations, Kits and Routes of Administration

Therapeutic compositions comprising mesenchymal cells as disclosed herein are also provided. Such compositions typically comprise the mesenchymal cells and a pharmaceutically acceptable carrier. The therapeutic compositions disclosed herein are useful for, inter alia, stimulating proliferation and differentiation of neural precursor cells and/or endothelial cells such as may be required following infarction, an ischemic injury, necrosis and traumatic injury. Accordingly, a "therapeutically effective amount" of a composition comprising mesenchymal cells can be any amount suitable for these purposes, and can be determined based on the nature and severity of the injury, the weight and general health of the subject and other criteria that are known to those of skill in the art. For example, dosage amounts can vary from about 100; 500; 1,000; 2,500; 5,000; 10,000; 20,000; 50;000; 100,000; 500,000; 1,000,000; 5,000,000 to 10,000,000 cells or more (or any integral value therebetween); with a frequency of administration of, e.g., a single dose, once per day, twice per week, once per week, twice per month, once per month, depending upon, e.g., body weight, route of administration, severity of disease, etc.

Various pharmaceutical compositions and techniques for their preparation and use are known to those of skill in the art in light of the present disclosure. For a detailed listing of suitable pharmacological compositions and techniques for their administration one may refer to texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

The mesenchymal cells described herein can be suspended in a physiologically compatible carrier for implantation. As used herein, the term "physiologically compatible carrier" refers to a carrier that is compatible with the other ingredients of the formulation and not deleterious to the recipient thereof. Those of skill in the art are familiar with physiologically compatible carriers. Examples of suitable carriers include cell culture medium (e.g., Eagle's minimal essential medium), phosphate buffered saline, Hank's balanced salt solution+/−glucose (HBSS), and multiple electrolyte solutions such as Plasma-Lyte™ A (Baxter).

The volume of a mesenchymal cell suspension administered to a subject will vary depending on the site of implantation, treatment goal and number of cells in solution. Typically the amount of cells administered will be a therapeutically effective amount. As used herein, a "therapeutically effective amount" or "effective amount" refers to the number of transplanted cells which are required to effect treatment of the particular disorder; i.e., to produce a reduction in the amount and/or severity of the symptoms associated with that disorder. Therapeutically effective amounts vary with the type and extent of injury, and can also vary depending on the overall condition of the subject.

The disclosed therapeutic compositions can also include pharmaceutically acceptable materials, compositions or vehicle, such as a liquid or solid filler, diluent, excipient, solvent or encapsulating material, i.e., carriers. These carriers can, for example, stabilize the mesenchymal cells and/or facilitate the survival of the mesenchymal cells in the body. Each carrier should be "acceptable" in the sense of being compatible with the other ingredients of the formulation and not injurious to the subject. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Exemplary formulations include, but are not limited to, those suitable for parenteral administration, e.g., intrapulmonary, intravenous, intra-arterial, intra-ocular, intra-cranial, sub-meningial, or subcutaneous administration, including formulations encapsulated in micelles, liposomes or drug-release capsules (active agents incorporated within a biocompatible coating designed for slow-release); ingestible formulations; formulations for topical use, such as eye drops, creams, ointments and gels; and other formulations such as inhalants, aerosols and sprays. The dosage of the compositions of the disclosure will vary according to the extent and severity of the need for treatment, the activity of the administered composition, the general health of the subject, and other considerations well known to the skilled artisan.

In additional embodiments, the compositions described herein are delivered locally. Localized delivery allows for the delivery of the composition non-systemically, thereby reducing the body burden of the composition as compared to systemic delivery. Such local delivery can be achieved, for example, through the use of various medically implanted devices including, but not limited to, stents and catheters, or can be achieved by inhalation, injection or surgery. Methods for coating, implanting, embedding, and otherwise attaching desired agents to medical devices such as stents and catheters are established in the art and contemplated herein.

Another aspect of the present disclosure relates to kits for carrying out the administration of mesenchymal cells to a subject. In one embodiment, a kit comprises a composition of mesenchymal cells, formulated as appropriate (e.g., in a pharmaceutical carrier), in one or more separate pharmaceutical preparations.

EXAMPLES

Example 1: Levels of Intracellular and Secreted FGF2 in MSCs and DNTT-MSCs

Cell extracts and conditioned medium from MSCs and DNTT-MSCs were prepared from cryopreserved cells. Cell aliquots were thawed, washed, resuspended in basal medium for embryonic neuronal cells (NeuroBasal, (NB), Life Technologies, Carlsbad, Calif.) and washed twice. Sources of MSCs and preparation of DNTT-MSCs have been described. See, for example, U.S. Pat. No. 7,682,825, in which MSCs are referred to as "bone marrow stromal cells" and DNTT-MSCs are referred to as "neural precursor cells;" and U.S. Patent Application Publication No. 2010/0266554, in which MSCs are referred to as "marrow adherent stem cells" and DNTT-MSCs are referred to as "neural regenerating cells." See also Aizman et al. (2009) *J. Neurosci. Res.* 87:3198-3206. The disclosures of all of the foregoing references are incorporated by reference herein, in their entireties, for the purposes of describing sources and methods of production for MSCs and DNTT-MSCs.

For preparation of cell-free extracts designated as E0, $2\times10^6$ cells were frozen in 4 ml of NB at $-80°$ C. for 1-2 hours, then thawed, resuspended in a total of 10 ml NB medium, and the suspension was cleared by centrifugation at 3000 rpm for 15 min. This process essentially ruptures the cell membrane, resulting in release of intracellular contents. The supernatants were distributed into aliquots and stored at $-80°$ C.

For preparation of conditioned medium (CM), $2\times10^6$ cells were plated into a T75 flask, in α-minimal essential medium (Mediatech, Inc, Manassas, Va.) supplemented with 10% fetal bovine serum (HyClone, Logan, Utah) and penicillin/streptomycin (αMEM/FBS/PS) (Life Technologies) and cultured overnight. Next day, the medium was changed to NB for 1 h, then discarded and replaced with 10 ml of fresh NB, and culture was continued for 24 hrs.; after which the conditioned medium was removed, centrifuged at 3000 rpm for 15 min, distributed into aliquots, and stored at $-80°$ C.

Following removal of conditioned medium, the flask from which the medium was removed (containing a layer of cells) was frozen and thawed, cell remnants were extracted with 10 ml NB, the extract was centrifuged, and the supernatants were distributed into aliquots and stored at $-80°$ C. These cell-free extracts were designated E1 extracts. Preliminary experiments indicated that no cells survived the freeze/thaw procedure. Unless indicated otherwise, E0s and CMs were produced using the same proportion of cells to medium: 1 million cells/5 ml NB.

Levels of FGF2 (bFGF) and other cytokines were measured by ELISA. Quantikine® Immunoassays for basic FGF (FGF2), high-sensitivity (HS) basic FGF, VEGF and acidic FGF (FGF1) were obtained from R&D Systems (Minneapolis, Minn.). The MCP-1 ELISA kit was obtained from Boster Biological Technology (Pleasanton, Calif.). ELISAs were performed according to manufacturers' instructions, except that for FGF2 ELISAs the samples were incubated overnight. This provided results that were comparable to those obtained with a 2 hour-incubation, as recommended by the manufacturer. Optimal dilutions for FGF2 detection, as determined in preliminary experiments, were 1/10 for E0 extracts and 1/2 or no dilution for CM.

Intracellular FGF2 levels in MSCs and DNTT-MSCs were determined by assaying for FGF2 in cell-free extracts of cells subjected to a single freeze/thaw cycle (E0 extracts). Cells were obtained from 7 donors and the results were averaged. FIG. 1A shows that one million MSCs release an average of 3.9 ng of FGF2; while one million DNTT-MSCs release an average of 7.2 ng of FGF2. One freeze/thaw cycle was sufficient to kill all the cells (as tested with Trypan blue staining and cell plating), while each additional freeze/thaw cycle decreased FGF2 concentration by about 20%.

By contrast, CM obtained from the same number of either MSCs or DNTT-MSCs contained approximately 0.02 ng of FGF2 (FIG. 1B). Thus, MSCs and SB623 cells contain a large intracellular reservoir of FGF2, but secrete very little of it.

To control for potential differences in cell metabolic activity, LDH activity (a surrogate marker for cell number) was measured in cell-free extracts of washed cryopreserved MSCs and DNTT-MSCs (E0 extracts), and in cell-free extracts obtained after cell growth and production of CM (E1 extracts). Activity was detected in cell extracts at 1:2 and 1:4 dilutions using a LDH Cytotoxicity Detection Kit (Clontech Laboratories, Mountain View, Calif.) and averaged. Bovine LDH (Sigma Aldrich, St. Louis, Mo.) was used as a standard.

Figure 1C:
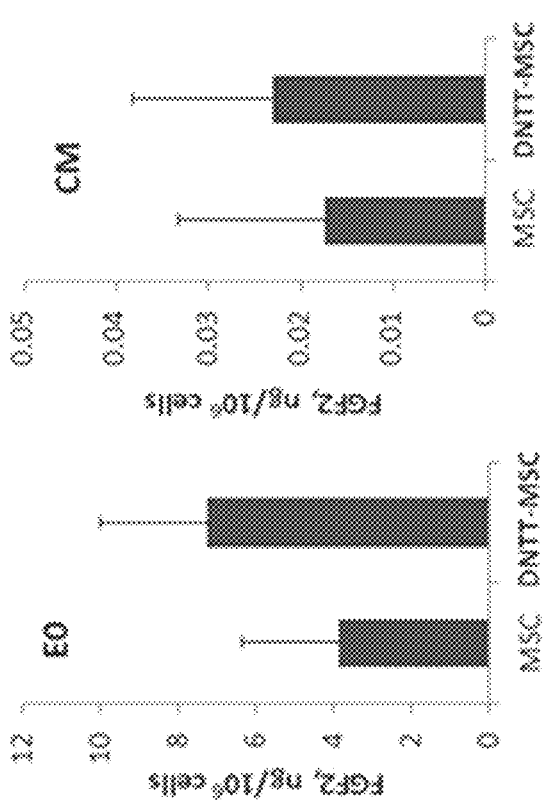

Results of the LDH assays showed that, for both MSCs and DNTT-MSCs, LDH activity was higher in E0 extracts (0.3 U/$10^6$ cells) than in E1 extracts (0.13 U/$10^6$ cells); indicating that metabolic activity dropped in starving cells compared to cells ruptured after cryopreservation (FIG. 1C). However, levels of LDH were similar in E0 extracts from MSCs and DNTT-MSCs (approx. 0.3 U/$10^6$ cells) and in E1 extracts from MSCs and DNTT-MSCs (0.13 U/$10^6$ cells), indicating similar metabolic levels (i.e., similar cell numbers), both before and after culturing to produce CM, in both cell types (FIG. 1C).

These results indicate that, in MSCs and DNTT-MSCs, FGF2 is predominantly intracellular, while very little is secreted. The cellular distribution of FGF1, vascular endothelial growth factor (VEGF) and monocyte chemoattractant protein-1 (MCP1) were also investigated. Intracellular compartmentalization also appeared to be the case, in MSCs, for FGF1, but not for VEGF and MCP1 (Table 1).

TABLE 1

Detection of various factors in
CM and freeze/thaw (E0) extracts from MSCs

| | CM | | E0 | | Fold |
|---|---|---|---|---|---|
| | Average ng/$10^6$ cells | CV, % | Average ng/$10^6$ cells | CV, % | Difference (E0/CM) |
| FGF2 | 0.017 | 94 | 3.9 | 64 | 230 |
| FGF1 | LLD | — | 1.1 | 49 | — |
| VEGF | 0.4 | 121 | 0.002 | 23 | 0.005 |
| MCP1 | 0.003 | 85 | 0.001 | 89 | 0.3 |

Amounts of factors produced by 1 million MSC, determined by ELISA. Average measurements of 7 cell lots are shown for FGF2 and of 2 cell lots for other factors. LLD: lower limit of detection; CV: coefficient of variation.

FGF2 levels were also measured in freeze/thaw (i.e., E0) extracts from other human mesenchymal cells (human foreskin fibroblasts, HFF) and human umbilical vein endothelial cells (HUVEC)) and in human non-mesenchymal cells (i.e., the neural precursor cell (NPC) lines ENStem and ReNcell). As shown in Table 2, HFF released more FGF2, while HUVECs and human neural stem cell lines released less FGF2, than MSC.

TABLE 2

FGF2 content in extracts from different cell types

| | Average ng/$10^6$ cells | Standard deviation | n lots |
|---|---|---|---|
| Human NPC lines | 0.5 | 0.08 | 2 (ReNcell, ENStem) |
| HUVEC | 0.7 | 0.04 | 2 |
| HFF | 8.9 | 1.1 | 2 |
| MSC | 3.9 | 2.5 | 7 |
| DNTT-MSCs | 7.2 | 2.7 | 7 |

Example 2: Extracts of MSCs Promote Proliferation of Neural Precursor Cells

Rat embryonic cortical cell populations contain a large proportion of neural precursor cells (NPCs) that proliferate in response to FGF2. The biological effects of intracellular FGF2 in MSCs was characterized by contacting rat cortical cells with dilutions of MSC-derived E0 and CM varying from 0 to 75% and conducting proliferation assays using BRDU incorporation.

The cortical cell assay has been described. See, for example, Aizman et al. (2013) Stem Cells Transl. Med. 2:223-232 and U.S. Patent Application Publication No. 2013/0210000 (Aug. 15, 2013). Briefly, ninety six-well plates (Corning Inc, Corning, N.Y.) were coated with Ornithine/Fibronectin (Orn/Fn, both from Sigma Aldrich, St. Louis, Mo.). Rat embryonic E18 cortex pairs were purchased from BrainBits (Springfield, Ill.); and the neural cells isolated as described by Aizman et al., supra. Assay medium consisted of NB supplemented with B27 and 0.5 mM L-alanyl-L-glutamine (GlutaMAX) (NB/B27/GLX, all from Invitrogen). Neural cells were plated at 6.7×$10^3$ cells/well; then various concentrations (0%-75% range) of E0 or CM were added to wells, in triplicate. In antibody neutralization experiments, neutralizing anti-FGF2 antibody clone bFM1 (Millipore, Billerica, Mass.) or control Mouse IgG (R&D Systems, Minneapolis, Minn., USA) were also added, each at 2 ug/ml. Wells containing medium, but no cells, were used as blank. Following addition of extracts, neural cells were cultured for 5 days.

To quantify proliferation, 5-bromo-2'-deoxyuridine (BRDU) labeling was carried out for 2 hrs and the plates were then processed using Cell Proliferation ELISA, BrdU (Colorimetric) (Roche Diagnostics GmbH, Mannheim, Germany) according to the manufacturer's instructions. Standards were made by serial dilutions of the anti-BRDU reagent starting from 1:1000. The highest standard value was arbitrarily set as 100 and results of colorimetric analyses were expressed in these units. Color development was quantified using SpectraMax Plus plate reader (Molecular Devices, Sunnyvale, Calif.).

Figure 2B:
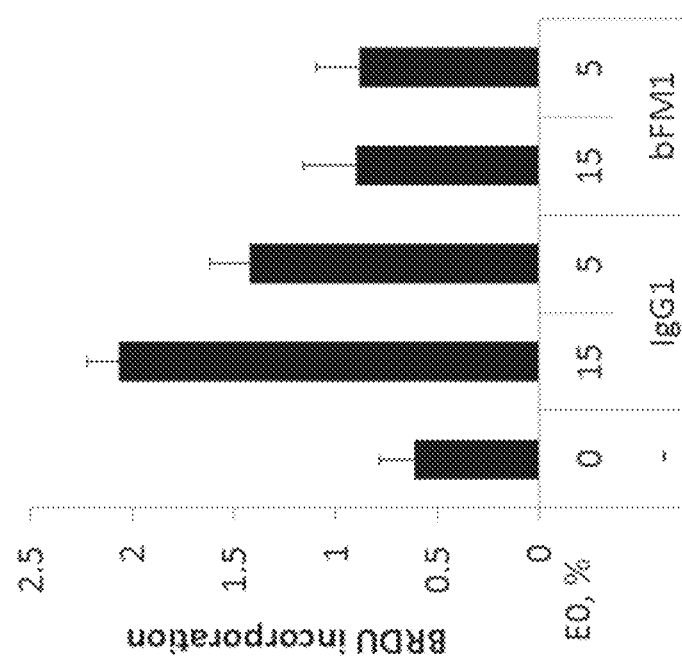
FIGS. 2A and 2B show measurements of neural cell proliferation assayed by BRDU incorporation.
Figure 2A:
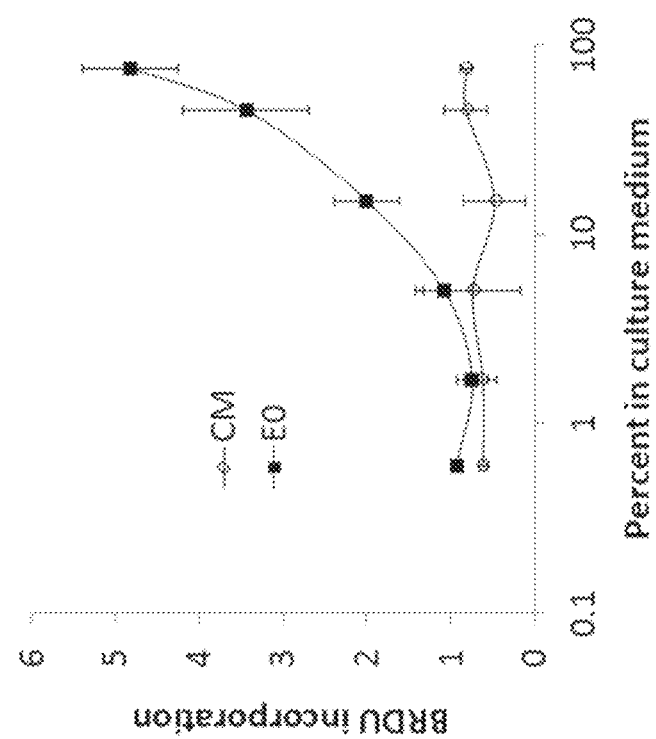

The results of these experiments showed that treatment of neural cells with the E0 cell-free extract from MSCs increased neural cell proliferation in a dose-dependent fashion; while treatment of neural cells with MSC conditioned medium (i.e., secreted molecules) had no effect on proliferation (FIG. 2A). In additional experiments, it was shown that the proliferative response to E0 extract from DNTT-MSCs was diminished in the presence of the neutralizing anti-FGF2 (bFM1) antibody, while the control antibody had no effect (FIG. 2B). Thus, intracellular FGF2 released from MSCs and DNTT-MSCs promotes proliferation of neural cells.

Figure 12:
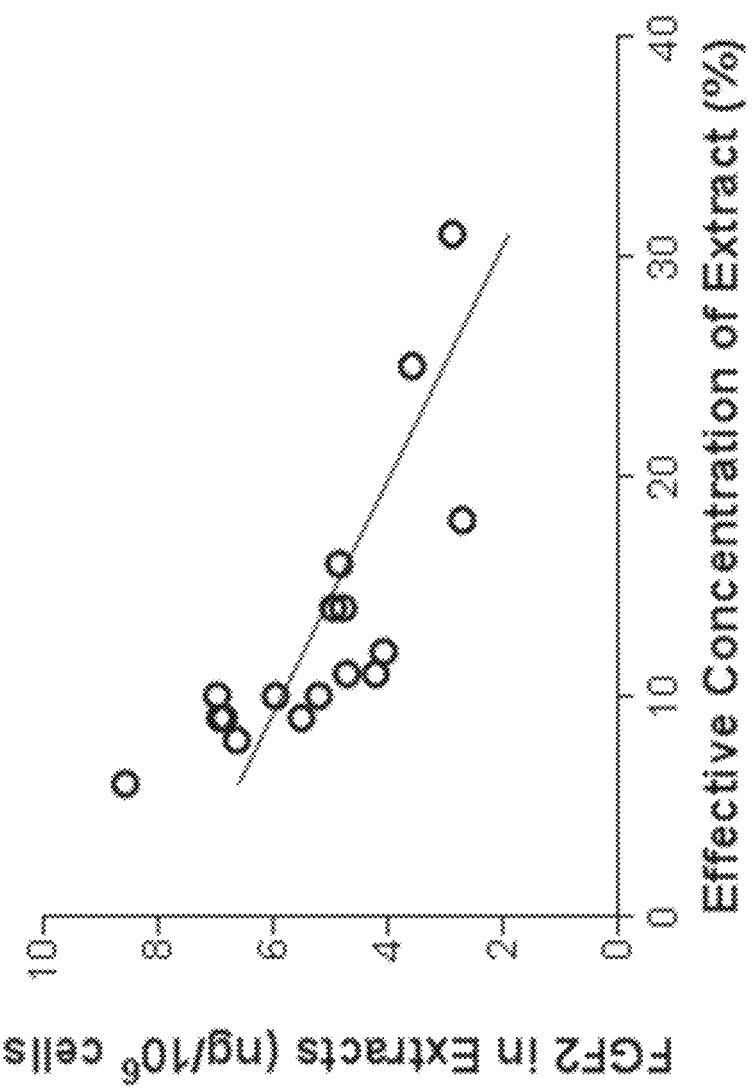
FIG. 12 shows the relationship between FGF2 levels in cell-free E0 extracts from DNTT-MSCs and the effective concentration of extract that provides three-fold stimulation of proliferation of neural precursor cells.

Additional support for the role of intracellular FGF2 in stimulating neural precursor cell proliferation is shown in FIG. 12. In this experiment, E0 extracts from different lots of DNTT-MSCs were assayed for FGF2 content by ELISA (as described in Example 1) and dilutions of these E0 extracts were tested in the proliferation assay described above. For each lot of cells, the effective concentration of extract (after dilution) which stimulated cell proliferation three-fold above background (no extract) was then plotted against the FGF2 concentration in that extract. The results show an inverse correlation between FGF 2 content and the effective concentration of extract required for three-fold stimulation of proliferation; i.e., a direct correlation between FGF2 levels in the extract and the ability to stimulate proliferation.

In addition to neural precursor cells, the embryonic rat cortical cell population contains immature neurons. To identify which subpopulation(s) of cells proliferated in response to MSC and DNTT-MSCs extracts, neural cells were cultured with or without E1 extracts (i.e., cell-free extracts obtained from cells that had been cultured to provide conditioned medium) from DNTT-MSCs for 5 days and then immunostained for dcx (a marker for immature neurons) and nestin (a neural precursor cell marker), and also labeled with BRDU. Analysis of immunostaining revealed that, in extract-treated cultures, there was no increase in $DCX^+$ or $BRDU^+/DCX^+$ cells; in contrast, there was a dramatic increase in nestin-positive cells; and practically all nestin-positive cells were also BRDU-positive. These results indicate that, after 5 days of culture, neural precursor cells were the major cell subpopulation that proliferated in response to the extracts.

Example 3: Extracts of MSCs and DNTT-MSCs Promote Proliferation of Endothelial Cells In light of the reported angiogenic activity of FGF2, extracts of MSCs and DNTT-MSCs were tested for their ability to induce proliferation of human umbilical vein endothelial cells (HUVEC). For these experiments, HUVEC were cultured in endothelial growth medium, EGM™ supplemented with Bovine Brain Extract (both from Lonza) and 2% FBS for 2-4 passages, distributed into aliquots, and stored cryopreserved. For the assay, 96-well plates were coated with 40 μg/ml of Rat tail Collagen I (Life Technologies) for 2 hours, then aspirated, dried, and washed or stored at −20° C. until use. The assay medium was Medium 199 (Life Technologies) supplemented with 0.5% FBS. HUVEC, either freshly thawed or after overnight culturing, were plated at $2.5 \times 10^3$ cells/well in the presence of various dilutions of extracts and CM, using NB alone as a negative control, in triplicates. In some experiments, the anti-FGF2 antibody bFM1 or control mouse IgG1 were included (each at a concentration of 2 μg/ml) in the presence of 15% E0 extract from DNTT-MSCs (containing approximately 0.2 ng/ml FGF2). In additional experiments, recombinant human VEGF165 (rVEGF) (R&D Systems) or recombinant FGF2 (rFGF2) (Peprotech, Rocky Hill, N.J., USA) were included in place of extract or CM, at concentrations of 10 ng/ml and 1 ng/ml, respectively. After 2 days of culture, cells were labeled with BRDU for 2 hours; and BRDU incorporation was quantified as described in Example 2.

The results are shown in FIG. 3. The MSC E0 extract strongly induced proliferation of HUVEC, while MSC-CM and NB medium had no effect (FIG. 3A). In a separate experiment, HUVEC were incubated with rVEGF, rFGF2, or DNTT-MSCs-E0 extract (15%) with or without FGF2-neutralizing and control antibodies (FIG. 3B). The response to E0 extract was inhibited by the anti-FGF2 neutralizing antibody bFM1, but not by control mouse IgG1, indicating that HUVEC proliferation in this assay was driven by FGF2. Notably, the activity of both native and recombinant FGF2 was similar in this assay; indeed, when the background (no E0 extract, no recombinant growth factor, FIG. 3B, leftmost bar) was subtracted, the response induced by 15% E0 extract (which corresponded to a final FGF2 concentration of 0.2 ng/ml in this E0 preparation) was approximately 4 times less than the response induced by 1 ng/ml rFGF2.

Example 4: Neurogenic Activity of Live Cells, Dead Cells and Cell Extracts

A quantitative assay for neurogenic and gliogenic factors (described in co-owned U.S. Patent Application Publication No. 2013/0210000) was used to characterize neuropoietic activities in MSCs and DNTT-MSCs. This assay was used to (a) assess the activity of extracts and (b) compare the activity of extracts with the activity of live and dead cells. For these experiments, a working suspension of either MSC or DNTT-MSCs in NB was divided into 3 aliquots. One aliquot received no further treatment and was designated live cells (denoted "A"). The remaining two aliquots were frozen and then thawed, which yielded cell lysates (i.e., dead cells, denoted "D"). One of these two cell lysates was then cleared by centrifugation to yield a cell-free extract (denoted "E").

The neuropoiesis assay utilized CellBIND Surface 96-well plates (Corning) coated with MSC-derived ECM as a substrate for cell growth. Each of the 3 aliquots (live cells, dead cells and cell-free extracts) were plated at identical dilutions, which corresponded to 500, 250, or 125 live MSC or DNTT-MSCs/well. Cortical cells (5000 cells/well) were added to all wells. After culturing, expression of rat nestin, rat glial fibrillary acidic protein (GFAP), and human glyceraldehyde phosphate dehydrogenase (GAP) were quantified by qRT-PCR, using a Taqman assay (Life Technologies).

The results are shown in FIG. 4. Confirming previous results (Example 2, above), nestin expression was induced by cell-free extracts; but to a lesser degree than by live cells or cell lysates (FIG. 4A). The cell lysate induced slightly stronger Nestin expression than did the suspension of live cells. In contrast, GFAP expression was induced by live cells, but not by cell-free extracts, and only slightly by cell lysates (FIG. 4B). The lack of human GAP expression in cultures treated with cell lysates confirmed the absence of surviving human cells (FIG. 4C).

The differences in the abilities of cell-free extracts, live cells and cell lysates to induce nestin expression might be explained by the prior observation that coculture of neural cells with MSCs triggers incremental nestin expression by supporting the proliferation of Nes$^+$GFAP$^+$ precursors. Aizman et al. (2013) *Stem Cells Transl Med.* 2:223-232. While soluble cell-free extracts are an abundant source of cytosolic FGF2, cell lysates also contain cell remnants (nuclei, for example), which may release additional FGF2 and provide further stimulation of cell proliferation and nestin expression.

Finally, it should be noted that the cell-free extracts used in this experiment were 40-fold more dilute than the E0 extracts used in the experiments described above: indeed, the most concentrated extract used in these experiments (i.e., extract from 500 cells in 100 μl culture medium) corresponds to a 2.5% dilution of E0 prepared as described above ($10^6$ cells/5 ml medium).

Example 5: Induction of Glial Cell Precursors

Following intracerebral implantation, it is not uncommon for the majority of grafted cells to die shortly afterward. Accordingly, combinations of live DNTT-MSCs and dead DNTT-MSCs (i.e., DNTT-MSC cell lysates), prepared as described in Example 4 above, were tested in the neuropoiesis assay described in Example 4. To this end, cell lysates (i.e., dead cells, D) and live cells (A) were mixed, in a 3:1 ratio of dead cells to live cells, and the activity of this mixed sample was compared to that of samples containing the same total cell number of either dead cells or live cells.

As expected from the results described in Examples 2 and 4, nestin expression was induced similarly by all 3 samples. FIG. 4D shows that a mixture of dead and live cells had a synergistic effect on expression of glial fibrillary acidic protein (GFAP), an astrocyte marker. This synergy was observed with both MSC- and DNTT-MSC-derived samples. Synergism between dead cell and live cell samples was not due to presence of excess live human cells in mixed D/A preparations, since similar human GAP levels were detected in both the live cell samples and the dead cell/live cell mixtures (FIG. 4E). Thus, live MSC or DNTT-MSCs, their extracts, or suspensions of cells killed by a single freeze/thaw cycle could all promote neural precursor growth; while robust astrogenesis required the presence of live MSCs or DNTT-MSCs.

Example 6: Release of Intracellular FGF2 from MSCs and DNTT-MSCs Resulting from the Cytotoxic Activity of PBMCs When cells are injected into the brain, damage to small brain vessels can occur; and this disruption of the vasculature may result in exposure of the implanted cells to local peripheral blood mononuclear cells (PBMCs) and their associated cytotoxic effects. To test whether intracellular stores of biologically active FGF2 could be released from MSCs and DNTT-MSCs by the naturally-occurring process of PBMC cytotoxicity; PBMC-mediated cell lysis, and release of FGF2, were assessed in 18 hour-cocultures of PBMCs (pre-cultured for 7 days in the absence of IL2) and target cells (either MSCs or DNTT-MSCs).

For these assays, PBMCs were obtained from buffy coat preparations of whole blood, using Ficoll-Paque Plus (GE Healthcare, Uppsala, Sweden) according to the manufacturer's instructions. The lymphocyte/monocyte/platelet fraction was collected and washed by centrifugation (600 rpm for 20 min) to remove the majority of platelets. Effector cells (PBMCs) were cultured for 7 days prior to co-culture with target cells (MSCs or DNTT-MSCs) at 10- or 30-fold excess of PBMCs to target cells for 18 hrs. Control cultures contained PBMCs only, MSCs only, DNTT-MSCs only, and medium only. MSCs and DNTT-MSCs were also plated separately and lysed by the addition of Triton to a final concentration of 1% (w/v) to the cultures during the final 30 min of culture, for determination of total LDH activity in target cells. Five replicates of each condition were conducted.

After culturing, the plate was centrifuged at 1000 rpm for 5 min. From three of the five replicates, 25 µl of supernatant were removed from each well for measurement of LDH activity using a LDH Cytotoxicity Detection Kit (Clontech Laboratories, Mountain View, Calif.). Cytotoxicity was expressed as "specific release of LDH activity" in effector-target co-cultures, according to the formula:

$$\text{Percent specific release} = \frac{(LDH \text{ release by target cells in co-culture}) - (LDH \text{ release by target cell cultured alone}) - (LDH \text{ release by effector cells cultured alone})}{(\text{total } LDH \text{ in target cells released by } Triton \text{ lysis}) - (LDH \text{ release by target cell cultured alone})} \times 100.$$

Supernatant (10-50 µl, depending on expected concentration of FGF2) was removed from the remaining two samples for measurements of FGF2, using a FGF2 Quantikine assay (R&D Systems, Minneapolis, Minn.). Specific FGF2 release from target cells in co-cultures was calculated in the same fashion as was specific release of LDH; i.e., as percentage of total FGF2 in target cells; and accounting for spontaneous background FGF2 release from target cells and effector cells.

Figure 5A:
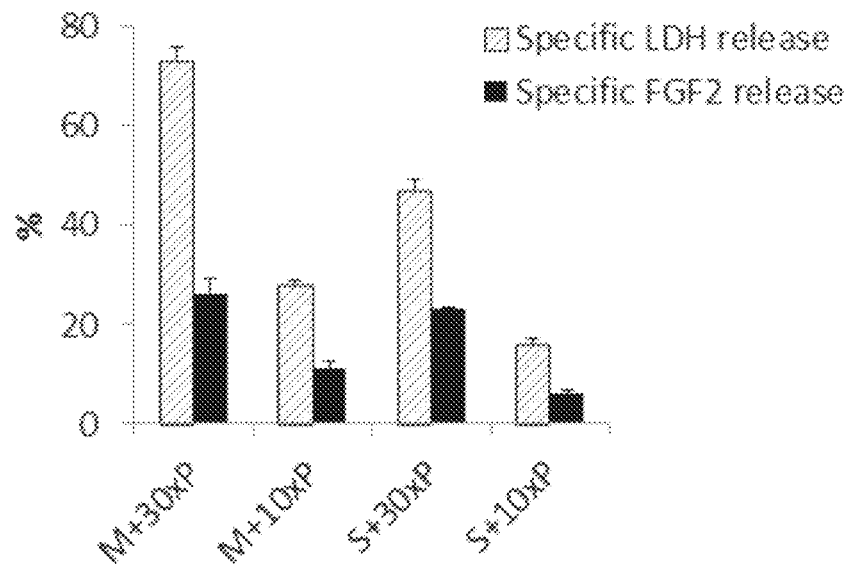
FIGS. 5A and 5B show degree of cell lysis (measured by release of LDH) and FGF2 release from MSCs and DNTT-MSCs that were co-cultured with PBMCs.

Representative results are shown in FIG. 5A. Lysis of MSCs and DNTT-MSCs, as measured by specific LDH release, was proportional to effector cell:target cell ratios, and varied from 30 to 90% at a 30:1 PBMC:target cell ratio for different donors of MSCs, DNTT-MSCs, and PBMCs. Percentage release of FGF2 from target cells correlated with the degree of lysis, although the percentage of specific FGF2 release was lower than that of LDH by about 2-2.5 fold.

Figure 5B:
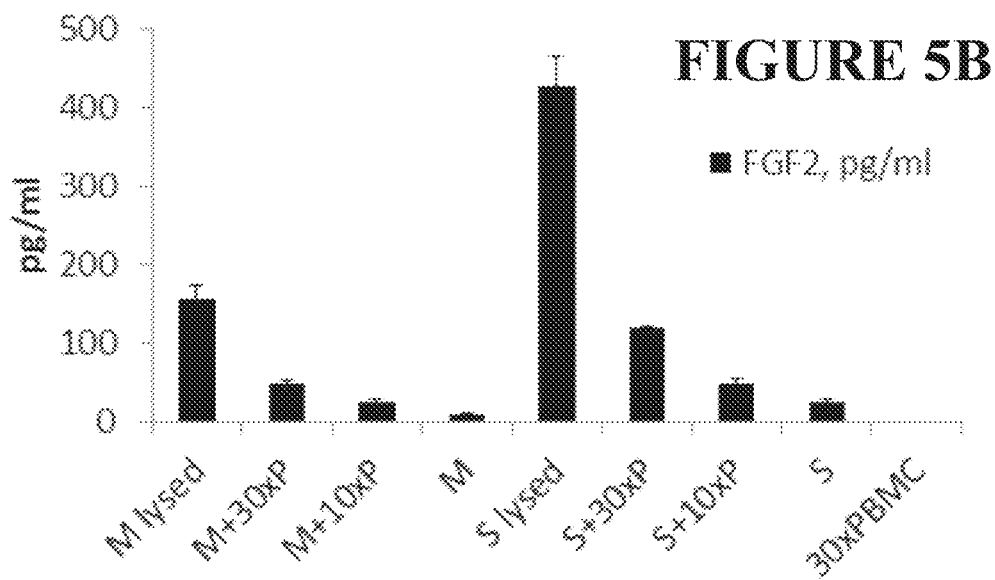

Although in this experiment specific lysis in MSC/PBMC co-cultures was higher than that in DNTT-MSC/PBMC co-cultures (FIG. 5A), more FGF2 was released in DNTT-MSCs co-cultures, due to higher intracellular levels of FGF2 in DNTT-MSCs (FIG. 5B, compare "S lysed" with "M lysed" samples). In addition, DNTT-MSCs release more FGF2 in the absence of PBMCs than do MSCs (FIG. 5B, compare "S" and "M" samples.

In conclusion, these results indicate that substantial amounts of FGF2 can be released by both MSCs and DNTT-MSCs as a result of the cytotoxic effects of PBMCs.

Example 7: FGF2 is Released from MSCs and DNTT-MSCs in High-Density, Hypoxic, Nutrient-Poor Cultures When cells are implanted into a zone of tissue injury (e.g., secondary to infarction), they are deposited at high density into an often hypoxic environment characterized by limited diffusion of oxygen and nutrients. To model the intracerebral microenvironment post-implantation, MSCs or DNTT-MSCs were plated in round-bottom wells of a 96-well plate in NB/B27/GLX at a concentration of $0.35 \times 10^6/350$ µl/well. The wells were tightly sealed with PCR tape to prevent gas exchange. The medium became rapidly acidic, indicating a hypoxic environment. The majority of cells remained non-adherent; however, even after 5 days of culturing in this environment, the cultures still contained a few living cells that, when re-plated under normal growth conditions, were able to attach, grow, and proliferate.

The contents of the wells were harvested at several time points, centrifuged to separate CM from cells and debris, and the cell pellets were subjected to a freeze/thaw cycle to release intracellular contents from surviving cells. Thus, at each time point, supernatants were collected (300 µl/well, designated here as CM), pellets were resuspended in 300 µl of NB; and both supernatant and resuspended pellets were frozen. After all time points had been collected, all samples were thawed and cleared by centrifugation (200 g for 10 min). LDH activity and FGF2 concentrations were then determined (as described in Example 6) in the CMs and in the freeze-thaw extracts of the cell pellets. In these experiments, CM and cell extracts were generated using 1 million cells/1 ml NB.

The results are shown in FIG. 6. Intracellular FGF2 content quickly dropped, in both MSCs and DNTT-MSCs, within 20 hours of initial plating, while levels of released FGF2 (in CM) remained steady between 4 h and 2 days (FIG. 6A). Substantially higher FGF2 levels were released from DNTT-MSCs, than from MSCs (around 2 vs. 0.5 ng/1 million cells, respectively). A decrease in the level of FGF2 in the CM was detected on day 5. The released FGF2 appeared stable for some time under the hypoxic culture conditions.

Release of LDH from MSCs and DNTT-MSCs increased over the course of hypoxic culture (FIG. 6B), as would be expected for a population of dying cells. However, intracellular LDH levels remained high as intracellular FGF 2 levels were dropping. This suggests that, under hypoxic conditions, surviving cells reduce their production of intracellular FGF2. In addition, DNTT-MSCs typically survived better than MSCs under these conditions, as indicated by higher levels of intracellular LDH in DNTT-MSCs at later time points.

Thus, while intracellular FGF2 is released from dying cells over the course of hypoxic culture, surviving cells appear to reduce their production of intracellular FGF2. Accordingly, implantation of an extract of cultured cells (MSCs or DNTT-MSCs) is likely to provide higher amounts of biologically-active FGF2 than implanted cells, which likely reduce their intracellular FGF2 stores following implantation.

Example 8: Synergy Between FGF2 and Additional Molecule(s) Released from DNTT-MSCs The effect of recombinant FGF2 (rFGF2, Peproptech, Rocky Hill, N.J.), alone and in combination with conditioned medium from DNTT-MSCs, on proliferation of rat embryonic cortical cells was assessed and compared with the effect of a DNTT-MSC freeze/thaw cell-free (E0) extract. Cell proliferation was measured as described in Example 2, above.

Figure 7A:
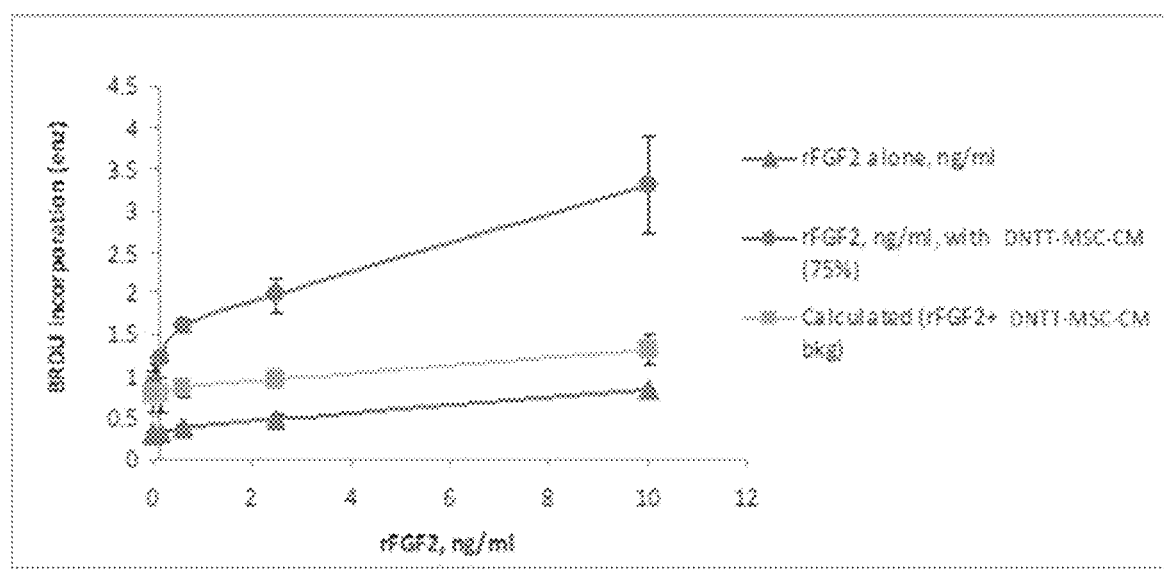
FIGS. 7A and 7B show measurements of neural cell proliferation assayed by BRDU incorporation.

FIG. 7A shows that rFGF has a slight stimulatory effect on cortical cell proliferation (FIG. 7A, triangles); however, the combination of rFGF2 and DNTT-MSC CM resulted in a much higher rate of proliferation (FIG. 7A, circles). This result indicates the presence of one or more components, in DNTT-MSC conditioned medium, that act in concert with FGF2 to stimulate cortical cell proliferation. Comparison to the calculated dose-response assuming an additive effect (FIG. 7A, squares) shows that the effect of rFGF2 and CM is synergistic.

The synergistic combination of rFGF2 and DNTT-MSC CM was compared to DNTT-MSC cell-free E0 extract in the cortical cell proliferation assay. For this experiment, cortical cells were exposed to different concentrations of rFGF2, alone or in combination with DNTT-MSC CM diluted to 75%, and to a series of dilutions of DNTT-MSC E0 extract. Assay of FGF2 levels in the E0 extract by ELISA indicated a FGF2 concentration of 3.5 ng/ml in undiluted E0 extract.

Figure 7B:
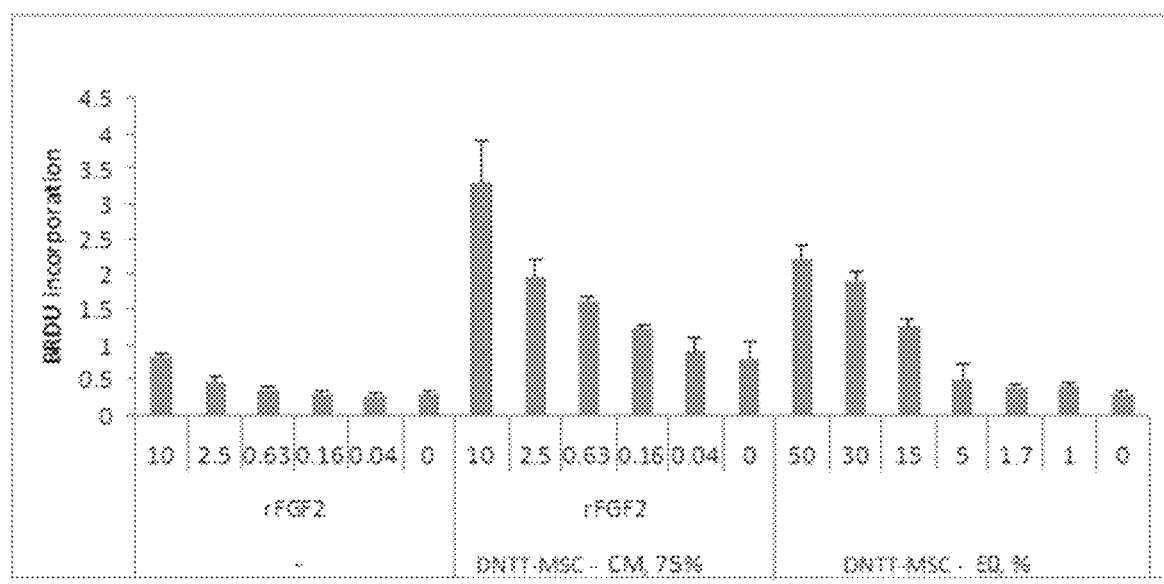

The results are shown in FIG. 7B. As previously noted, rFGF2 and CM acted synergistically to stimulate proliferation. The DNTT-MSC cell-free E0 extract also stimulated proliferation. Notably, half-strength E0 extract (containing approximately 1.75 ng/ml FGF2) had approximately the same proliferation-inducing activity as 2.5 ng/ml rFGF2 in the presence of conditioned medium (which generally contains no more that 20 pg/ml of FGF2).

These results indicate that DNTT-MSCs contain one or more molecules that act synergistically with FGF2 to stimulate proliferation of neural cells, and that such molecule(s) can be secreted.

Example 9: Characterization of Intracellular FGF2 in DNTT-MSCs

Figure 8:
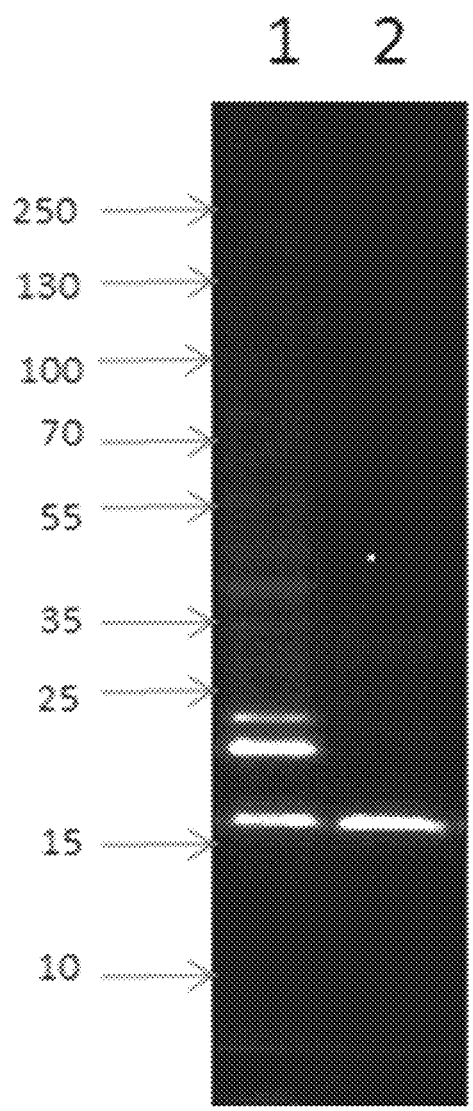
FIG. 8 shows analysis, by protein blotting, of intracellular FGF2 from DNTT-MSCs. FGF2 was identified, in blots of denaturing Tris-glycine polyacrylamide gels, using a bFM2 anti-FGF2 antibody (Millipore, Billerica, Mass.). Lane 1 contained a whole cell lysate from SB623 cells, obtained by lysing cells in a SDS-containing buffer. Lane 2 contained recombinant FGF2 (approx. 1 ng/ml). The positions of molecular weight markers, run in a separate lane of the gel, are shown to the left of lane 1.

Naturally-occurring FGF2 exists in at least five isoforms of 18 kD, 22 kD, 22.5 kD, 24 kD, and 34 kD. Recombinant FGF2 contains only the low molecular weight (18 kD) isoform (FIG. 8, lane 2). In contrast, whole-cell lysates of DNTT-MSCs prepared using RIPA buffer (Thermo Fisher Scientific, Rockford, Ill.) and analyzed on denaturing Tris-glycine SDS polyacrylamide gels comprises at least three FGF2 isoforms, as detected using a monoclonal anti-FGF2 antibody (bFM2, (Millipore, Billerica, Mass.) (FIG. 8, lane 1).

The intracellular distribution of the various FGF2 isoforms in DNTT-MSCs was investigated by analyzing various types of cell lysate and extract preparations. Total cell lysates from DNTT-MSCs were obtained by lysing cells in RIPA buffer (Thermo Fisher Scientific, Rockford, Ill.). This buffer contains both ionic and non-ionic detergents and solubilizes nuclear and cytoplasmic membranes, thereby releasing cytoplasmic, nuclear and membrane bound cellular components. Cytoplasmic lysates were prepared by lysing cells in an isotonic buffer, pelleting nuclei and cell debris and recovering the supernatant. The pellet obtained during preparation of the cytoplasmic lysate was extracted with RIPA buffer to yield a nuclear lysate. These lysates were compared with a cell-free E0 extract of DNTT-MSCs, prepared as described previously by subjecting cultured cells to a freeze/thaw cycle, then clearing by centrifugation. The E0 extract thus contains soluble cell components that are released by mechanical damage such as membrane rupture.

Figure 9:
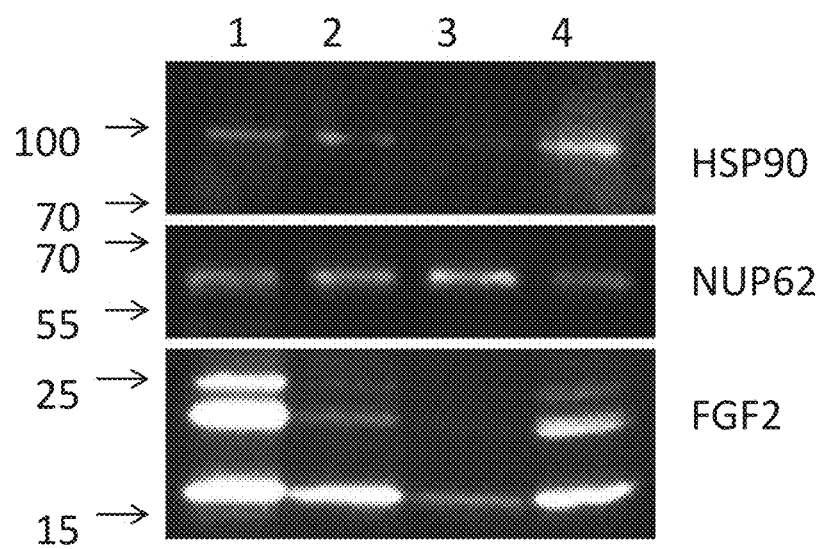
FIG. 9 shows the subcellular distribution of FGF2 isoforms in DNTT-MSCs, analyzed by protein blots of denaturing polyacrylamide gels. Lane 1 contained a total cell lysate from $3 \times 10^4$ DNTT-MSCs; lane 2 contained a cytoplasmic fraction from $1.5 \times 10^4$ DNTT-MSCs; lane 3 contained a nuclear fraction from $1.5 \times 10^4$ DNTT-MSCs; and lane 4 contained a cell-free E0 extract from $4 \times 10^4$ DNTT-MSCs. The positions of molecular weight markers, run in a separate lane of the gel, are shown to the left of lane 1. The upper panel shows levels of heat shock protein 90 (HSP90), a cytoplasmic marker, detected using an anti-hsp90 antibody (Boster Biologics, Pleasanton, Calif.). The middle panel shows levels of nucleoporin p62 (NUP62), a nuclear marker, detected using an anti-NUP62 antibody (Santa Cruz Biotechnology, Santa Cruz, Calif.). The lower panel shows levels of FGF2 isoforms, detected using the bFM2 anti-FGF2 antibody (Millipore, Billerica, Mass.).

Samples were analyzed by electrophoresis on a denaturing Tris-glycine-SDS polyacrylamide gel, and proteins were detected by immunoblotting. The results, shown in FIG. 9, indicate that the majority of FGF2 is present in the cytoplasm of DNTT-MSCs; and that the cell-free E0 extract contains primarily cytoplasmic material.

The fact that mesenchymal cells, such as DNTT-MSCs, contain several isoforms of FGF2 could explain the superior proliferation-inducing activity of DNTT-MSC extracts, compared to recombinant FGF2. See, for example, FIG. 7B, Example 8.

Example 10: Extracts of Fibroblasts Promote Proliferation and Differentiation of Neural Precursor Cells Human foreskin fibroblasts (HFF, ATCC 1041) were used to prepare freeze-thaw cell-free extracts and insoluble cell residue fractions as described in Example 1. Levels of FGF2 in these fractions, and in HFF cell lysates, were measured as described in Example 1, and the ability of these fractions to stimulate proliferation of neural cells was assayed as described in Example 2.

Figure 10A:
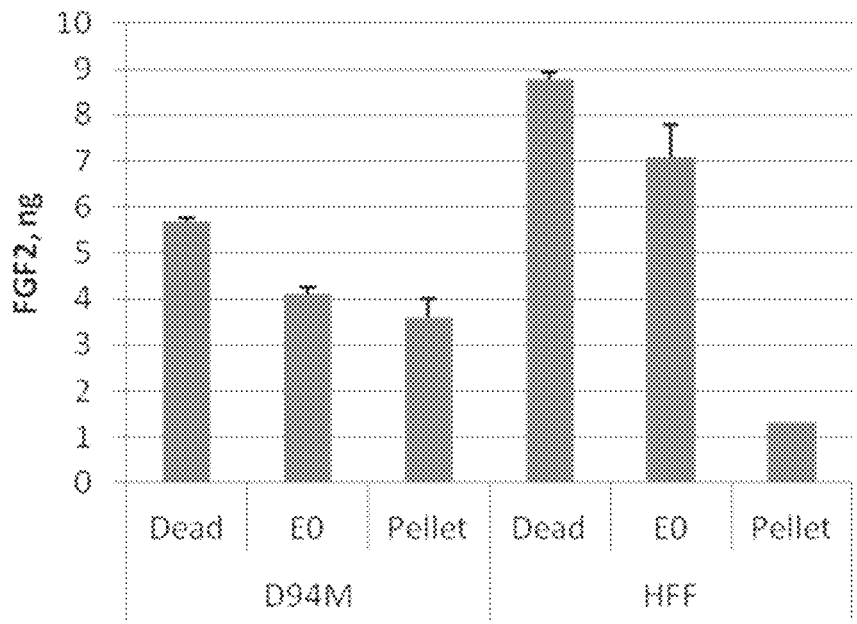
FIGS. 10A-10C show comparisons of MSC and human foreskin fibroblasts (HFF).
Figure 10B:
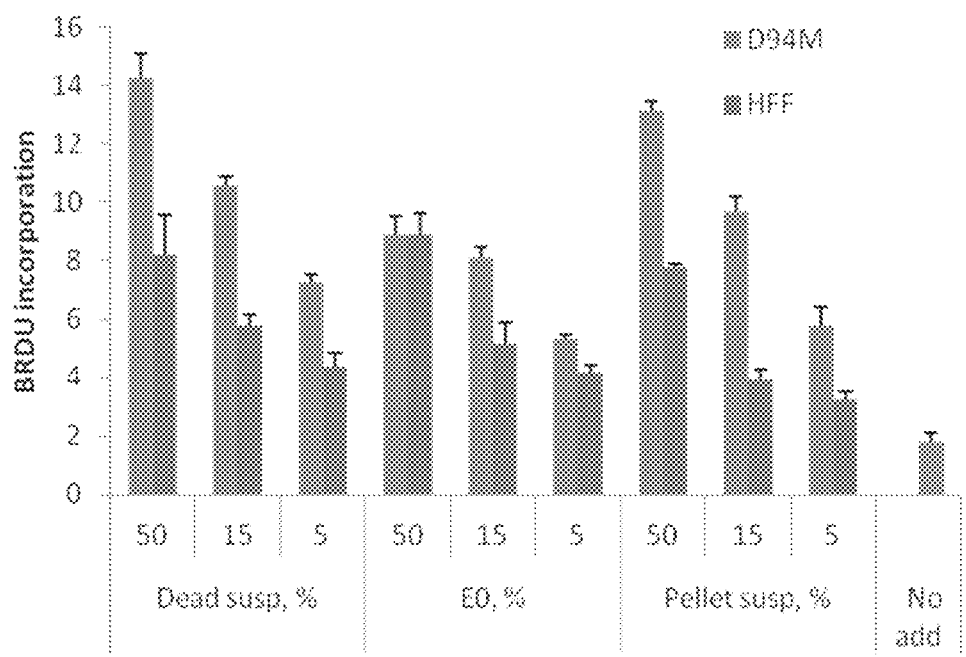
Figure 10C:
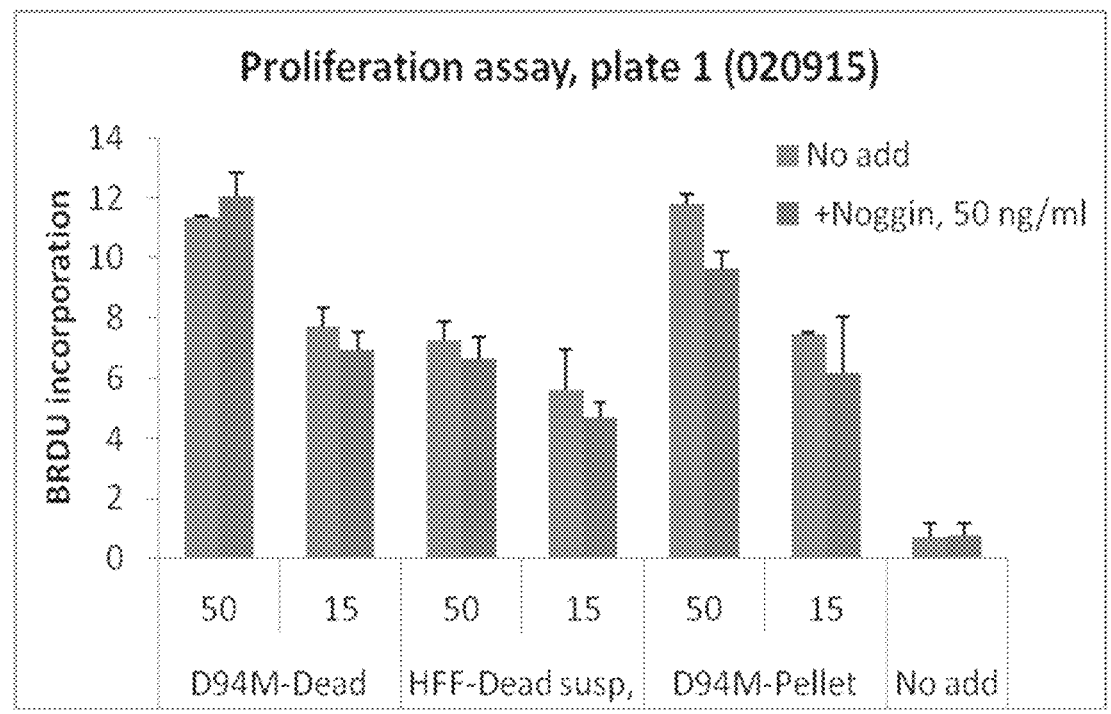

FIG. 10A shows that HFF contain somewhat higher levels of intracellular FGF2 than do MSCs. FIG. 10B shows that all fractions (cell lysate, cell-free (E0) extract, and cell residue) stimulate proliferation of neural precursor cells. The stimulatory effect of both HFFs and MSCs is insensitive to noggin, a BMP inhibitor (FIG. 10C). Since differentiation of astrocyte precursors is stimulated by BMPs, this result is consistent with proliferation of neuronal precursors.

Figure 11:
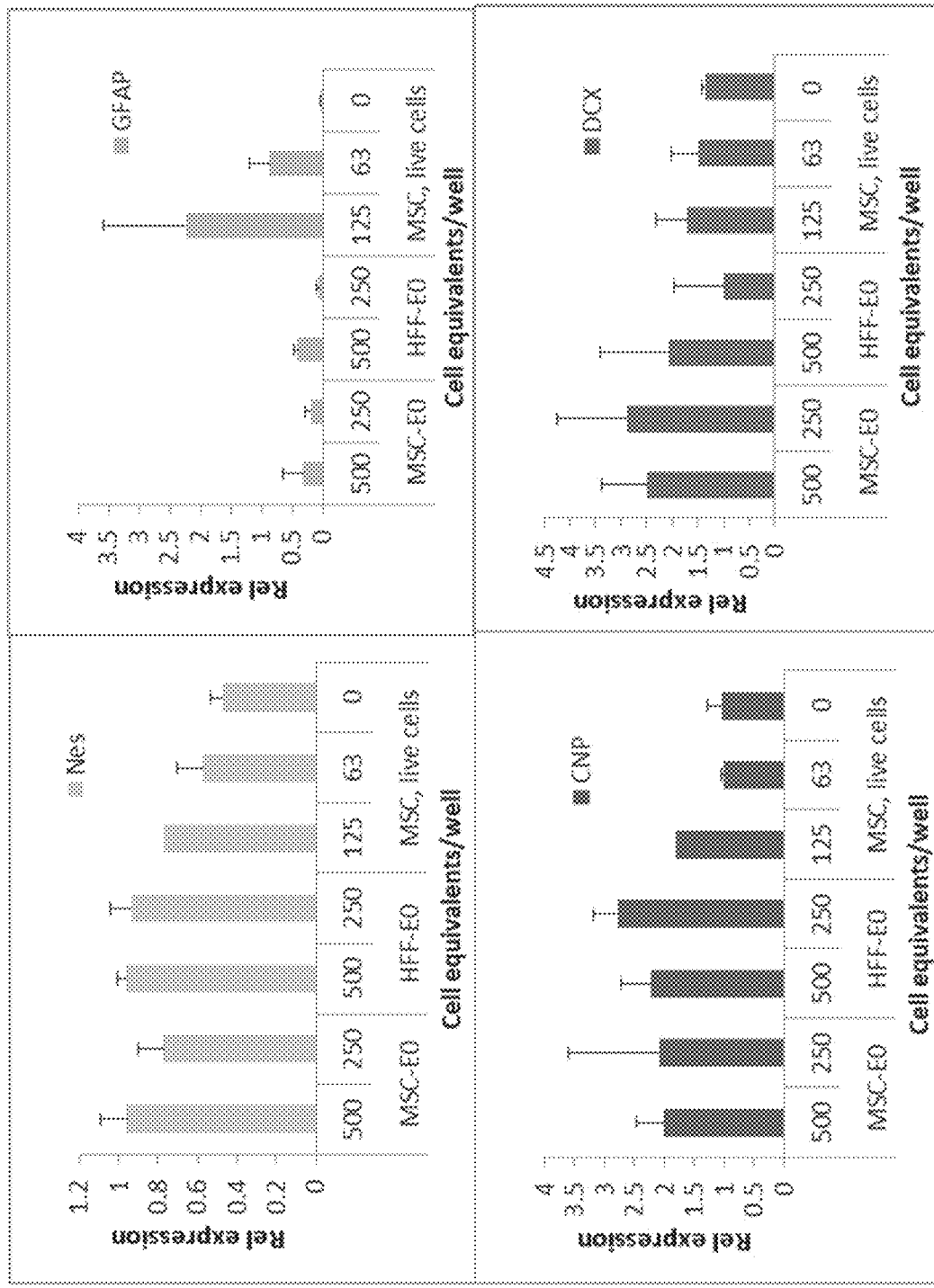
FIG. 11 shows levels of nestin (Nes, upper left panel), glial fibrillary acidic protein (GFAP, upper right panel), 2', 3'-cyclic nucleotide 3' phosphodiesterase (CNP, lower left panel) and doublecortin (dcx, lower right panel) in cultures of cortical cells exposed to live MSCs and cell-free freeze/thaw (E0) extracts from MSCs and HFFs.

Fractions from HFFs were also tested for their ability to promote differentiation of neural precursor cells, using the methods described in Example 4. The results, shown in FIG. 11, indicated that cell-free (E0) extracts from HFFs promoted differentiation of cortical cells into nestin-positive neural precursor cells, GFAP-positive astrocytes and CNP-positive oligodendrocytes.

REFERENCES

1. Caplan A I, Dennis J E: Mesenchymal stem cells as trophic mediators. *J Cell Biochem.* 2006, 98:1076-1084.
2. Joyce N, Annett G, Wirthlin L, Olson S, Bauer G, Nola J A: Mesenchymal stem cells for the treatment of neurodegenerative disease. *Regen Med.* 2010, 5:933-946.
3. Chen J, Venkat P, Zacharek A, Chopp M: Neurorestorative therapy for stroke. *Front Hum Neurosci.* 2014, 8:382.
4. Bang O Y, Lee J S, Lee P H: Autologous mesenchymal stem cell transplantation in stroke patients. *Ann Neurol.* 2005, 57:874-882.
5. Isakova I A, Baker K, Dufour J, Gaupp D, Phinney D G: *Preclinical evaluation of adult stem cell engraftment and toxicity in the CNS of rhesus macaques. Mol Ther.* 2006, 3:1173-1184.
6. Westrich J, Yaeger P, He C, Stewart J, Chen R, Selezik G, Larson 5, Wentworth B, O'Callaehan M, Wadsworth S, Akia G, Molnar G: Factors affecting residence time of mesenchymal stromal cells (MSC) injected into the myocardium. *Cell Transplant.* 2010, 19-937-848.
7. Chen L, Tredget E E, Liu C, Wu Y: *Analysis of allogenicity of mesenchymal stem cells in engraftment and wound healing in mice. PLoS One.* 2009, 4(9):e7119. doi: 10.1371/journal.pone.0007119.
8. Griffin M D, Ryan A E, Alagesan S, Lohan P, Treacy O, Ritter T: *Anti-donor Immune responses elicited by allogeneic mesenchymal stem cells: what have we learned so far? Immunol Cell Biol.* 2013, 91:40-51.
9. Coyne T M, Marcus A, Woodbury D, Black I B: Marrow stromal cells transplanted to the adult brain are rejected by an inflammatory response and transfer donor labels to host neurons and glia. *Stem Cells.* 2006 24:2483-2492.

10. Burns I C, Ortiz-González X R, Gutiérrez-Pérez M, Keene C D, Sharda R, Demorest Z L, Jiang Y, Nelson-Holte M, Soriano M, Nakagawa Y, Luquin M R, Garcia-Verduro J M, Prósper F, Low W C, Verfaillie C M: Thymidine analogs are transferred from prelabeled donor to host cells in the central nervous system after transplantation: a word of caution. *Stem Cells.* 2006, 24:1121-1127.

11. Yu P J, Ferrari G, Galloway A C, Mignatti P. Pintucci G: Basic fibroblast growth factor (FGF-2): the high molecular weight forms come of age. *J Cell Biochem.* 2007, 100:1100-1108.

12. Gajdusek C M, Carbon S: *Injury-induced release of basic fibroblast growth factor from bovine aortic endothelium. J Cell Physiol.* 1989, 139:570-579.

13. McNeil P L, Muthukrishnan L, Warder E, D'Amore P A: *Growth factors are released by mechanically wounded endothelial cells. J Cell Biol.* 1989, 109:811-822.

14. D'Amore P A: *Modes of FGF release in vivo and in vitro. Cancer Metastasis Rev.* 1990, 9:227-238.

15. Muthukrishnan L, Warder E, McNeil P L: Basic fibroblast growth factor is efficiently released from a cytosolic storage site through plasma membrane disruptions of endothelial cells. *J Cell Physiol.* 1991, 148:1-16.

16. Brunner G, Gabrilove J, Rifkin D B, Wilson E L: *Phospholipase C release of basic fibroblast growth factor from human bone marrow cultures as a biologically active complex with a phosphatidylinositol-anchored heparan sulfate proteoglycan. J Cell Biol.* 1991, 114:1275-1283.

17. Brunner G, Nguyen H, Gabrilove J, Rifkin D B, Wilson E L: Basic fibroblast growth factor expression in human bone marrow and peripheral blood cells. *Blood.* 1993, 81:631-638.

18. Benavente C A, Sierralta W D, Conget P A, Minguell J J: SubceHular distribution and mitogenic effect of basic fibroblast growth factor in mesenchymal uncommitted stem cells. *Growth Factors.* 2003, 21:87-94.

19. Aizman I, Tirumalashetty B J, McGrogan M, Case C C: *Comparison of the neuropoietic activity of gene-modified versus parental mesenchymal stromal cells and the identification of soluble and extracellular matrix-related neuropoietic mediators. Stem Cell Res Ther.* 2014, 5:29.

20. Dao M, Tate C C, McGrogan M, Case C C: *Comparing the angiogenic potency of naïve marrow stromal cells and Notch-transfected marrow stromal cells. J Transl Med.* 2013, 11:81.

21. Aizman I, Tate C C, McGrogan M, Case C C: *Extracellular matrix produced by bone marrow stromal cells and by their derivative. SB623 cells, supports neural cell growth. J Neurosci Res.* 2009, 87:3198-3206.

22. Tate C C, Fonck C, McGrogan M, Case C C: *Human mesenchymal stromal cells and their derivative, SB623 cells, rescue neural cells via trophic support following in vitro ischemia. Cell Transplant.* 2010, 19:973-984.

23. Aizman I, McGrogan M, Case C C: *Quantitative microplate assay for studying mesenchymal stromal cell-induced neuropoiesis. Stem Cells Transl Med.* 2013, 2:223-232.

24. Xiong Y, Mahmood A, Chopp M: *Angiogenesis, neurogenesis Ad brain recovery of function following injury. Curr Opin Investig Drugs.* 2010, 11:298-308.

25. Gonzalez A M, Carman L S, Ong M, Ray J, Gage F H, Shults C W, Baird A: *Storage, metabolism, and processing of 125I-fibroblast growth factor-2 after intracerebral infection. Brain Res.* 1994, 665:285-292.

26. Liekens S, Clercq E D, Neyts J: Angiogenesis: regulators and clinical applications. *Biochemical Pharmacology* 2001 61:253-270

27. Liew A, O'Brien T: Therapeutic potential for mesenchymal stem cell transplantation in critical limb ischemia. *Stem Cell Res Ther.* 2012, 3:28.

28. Madrigal M, Rao K S, Riordan N H: A review of therapeutic effects of mesenchymal stem cell secretions and Induction of secretory modification by different culture methods. *J Transl Med.* 2014, 12:260.

29. Witte L, Fuks Z, Haimovitz-Friedman A, Vlodavskv I, Goodman D S, Eldor A: Effects of Irradiation on the release of growth factors from cultured bovine, porcine, and human endothelial cells. *Cancer Res.* 1989, 49:5066-5072.

30. Hartnett M E, Garcia C M, D'Amore P A: Release of bFGF, an endothelial cell survival factor, by osmotic shock. *Invest Ophthalmol Vis Sci.* 1999, 40:2945-2951.

31. Benzaquen L R, Nicholson-Weller A, Halperin J A: Terminal complement proteins C5b-9 release basic fibroblast growth factor and platelet-derived growth factor from endothelial cells. *J Exp Med.* 1994, 179:985-992.

32. Cheng G C, Briggs W H, Gerson D S, Libby P, Grodzinsky A J, Gray M L, Lee R T: Mechanical strain tightly controls fibroblast growth factor 2 release from cultured human vascular smooth muscle cells. *Circ Res.* 1997, 80:28-36.

33. Fukuo K, Inoue T, Morimoto S, Nakahashi T, Yasuda O, Kitano S, Sasada R, Ogihara T: Nitric oxide mediates cytotoxicity and basic fibroblast growth factor release in cultured vascular smooth muscle cells: a possible mechanism of neovascularization in atherosclerotic plaques. *J Clin Invest.* 1995, 95:669-676.

34. Kave D, Pimental D, Prasad S, Mäki T, Berger H J, McNeil P L, Smith T W, Kelly R A: Role of transiently altered sarcolemmal membrane permeability and basic fibroblast growth factor release in the hypertrophic response of adult rat ventricular myocytes to increased mechanical activity in vitro. *J Clin Invest.* 1996, 97:281-291.

35. Clarke M S F, Caldwell R W, Chiao H, Miyake K, McNeil P L: Contraction-induced cell wounding and release of fibroblast growth factor in heart. *Circ Res.* 1995, 76:927-934.

36. Spaggiari G M, Capobianco A, Becchetti S, Mingari M C, Moretta L: *Mesenchymal stem cell-natural killer cell interactions: evidence that activated N K cells are capable of killing MSCs, whereas MSCs can inhibit IL-2-induced NK-cell proliferation.* Blood. 2006 107: 1484-1490.

37. Roemeling-van Rhijn M, Reinders M E, Franquesa M, Engela A U, Korevaar S S, Roelofs H, Genever P G, Ijzermans J N, Betjes M G, Baan C C, Weimar W, Hoogduijn M J: *Human Allogeneic Bone Marrow and Adipose Tissue Derived Mesenchymal Stromal Cells Induce CD8+ Cytotoxic T Cell Reactivity, J Stem Cell Res Ther.* 2013 3(Suppl 6):004.

38. Brumm K P, Perthen J E, Liu T T, Haist F, Avalon L, Love T: An arterial spin labeling investigation of cerebral blood flow deficits in chronic stroke survivors. *Neuroimage.* 2010, 51-995-1005.

39. Richardson J D, Baker J M, Morgan P S, Rorden C, Bonilha L, Fridriksson J. Cerebral perfusion in chronic stroke: Implications for lesion-symptom mapping and functional MRI. *Behav Neurol.* 2011, 24:117-122.

40. Ikeda N, Nonoeuchi N, Zhao M Z, Watanabe T, Kajimoto Y, Furutama D, Kimura F, Dezawa M, Coffin R S, Otsuki Y, Kuroiwa T., Mivatake S: Bone marrow stromal cells that enhanced fibroblast growth factor-2 secretion by herpes simplex virus vector improve neurological outcome after transient focal cerebral ischemia in rats. *Stroke* 2005 36:2725-2730.
41. Fujiwara K, Date I, Shingo T, Yoshida H, Kobayashi K, Takeuchi A, Yano A, Tamiya T, Ohmoto T: *Reduction of infarct volume and apoptosis by grafting of encapsulated basic fibroblast growth factor-secreting cells in a model of middle cerebral artery occlusion in rats. J Neurosurg.* 2003, 99:1053-1062.
42. Watanabe T, Okuda Y, Nonoguchi N, Zhao M Z. Kajimoto Y, Furutama D, Yukawa H. Shibata M A, Otsuki Y, Kuroiwa T, Mivatake S. Postischemic intraventricular administration of FGF-2 expressing adenoviral vectors improves neurologic outcome and reduces infarct volume after transient focal cerebral ischemia in rats. *J Cereb Blood Flow Metab.* 2004, 24:1205-1213.
43. Wang Z L, Cheng S M, Ma M M, Ma Y P, Yang J P, Xu G L, Liu X F: Intranasally delivered bFGF enhances neurogenesis in adult rats following cerebral ischemia. *Neurosci Lett.* 2008 446:30-35.
44. Li Q, Stephenson D: *Postischemic administration of bask fibroblast growth factor improves sensorimotor function and reduces infarct size following permanent focal cerebral ischemia in the rat. Exp Neurol.* 2002, 177:531-537.
45. Bogousslavsky J, Victor S J, Salinas E O, Pallay A, Donnan G A, Fieschi C, Kaste M, Orgogozo J M, Chamorro A, Desmet A; European-Australian Fiblast (Trafermin) in Acute Stroke Group: Fiblast (trafermin) In acute stroke: results of the European-Australian phase II/III safety and efficacy trial. *Cerebrovasc Dis.* 2002, 14:239-251.
46. Vu Q, Xie K, Eckert M, Zhao W, Cramer S C: *Meta-analysis of preclinical studies of mesenchymal stromal cells for ischemic stroke. Neurology.* 2014, 82:1277-1286.
47. Mishra P J, Mishra P J, Banerjee D: Cell-free derivatives from mesenchymal stem cells are effective in wound therapy. *World J Stem Cells.* 2012, 4: 35-43.
48. Parekkadan B, van Poll D, Suganuma K, Carter E A, Berthiaume F, Tilles A W, Yarmush M L: *Mesenchymal Stem Cell-Derived Molecules Reverse Fulminant Hepatic Failure. PLoS ONE* 2007, 2: e941.
49. Jiao J, Milwid J M, Yarmush M L, Parekkadan B: *A Mesenchymal Stem Cell Potency Assay. Methods Mol Biol.* 2011, 677:221-231.
50. Liu S, Jian L, Li H, Shi H, Luo H, Zhang Y, Yu C, Jin Y: Mesenchymal stem cells prevent hypertrophic scar formation via Inflammatory regulation when undergoing apoptosis. *J Invest Dermatol.* 2014, 134:2648-2657.

What is claimed is:

1. A method for inducing proliferation of a neural precursor cell (NPC); the method comprising providing FGF2 to the neural precursor cell; wherein the FGF2 is present in a preparation from a descendant of a mesenchymal stem cell (MSC) that has been transiently transfected with a vector comprising sequences encoding a Notch intracellular domain (NICD); wherein the preparation is selected from one or both of a soluble-cell-free extract and an insoluble cell residue.

2. The method of claim 1, wherein the FGF2 comprises a mixture of FGF2 isoforms.

3. The method of claim 2, wherein the FGF2 isoforms are selected from those having molecular weights of 18, 22, 22.5 and 24 kD.

4. The method of claim 2, wherein the mixture of FGF2 isoforms has greater biological activity than that of recombinant FGF2.

5. The method of claim 1, wherein the NPC is in a tissue that has undergone an ischemic injury.

6. The method of claim 5, wherein the ischemic injury is stroke.

7. The method of claim 1, wherein the NPC is in a tissue that is necrotic.

8. The method of claim 7, wherein necrosis in the tissue results from infarction or traumatic injury.

9. A method for inducing proliferation of an endothelial cell; the method comprising providing FGF2 to the endothelial cell; wherein the FGF2 is present in a preparation from a descendant of a mesenchymal stem cell (MSC) that has been transiently transfected with a vector comprising sequences encoding a Notch intracellular domain (NICD); wherein the preparation is selected from one or both of a soluble-cell-free extract and an insoluble cell residue.

10. The method of claim 9, wherein the FGF2 comprises a mixture of FGF2 isoforms.

11. The method of claim 10, wherein the FGF2 isoforms are selected from those having molecular weights of 18, 22, 22.5 and 24 kD.

12. The method of claim 10, wherein the mixture of FGF2 isoforms has greater biological activity than that of recombinant FGF2.

13. The method of claim 9, wherein the endothelial cell is in a tissue that has undergone an ischemic injury.

14. The method of claim 13, wherein the ischemic injury is stroke.

15. The method of claim 9, wherein the endothelial cell is in a tissue that is necrotic.

16. The method of claim 15, wherein necrosis in the tissue results from infarction or traumatic injury.

17. A method for stimulating proliferation of a neural precursor cell or an endothelial cell; the method comprising contacting the neural precursor cell or the endothelial cell with a combination comprising:
 (a) FGF-2, and
 (b) conditioned medium from a descendant of a mesenchymal stem cell (MSC) that has been transiently transfected with a vector comprising sequences encoding a Notch intracellular domain (NICD);
 wherein the neural precursor cell or endothelial cell is in a tissue that is necrotic; and
 wherein necrosis in the tissue results from infarction or traumatic injury.

18. A preparation, from mesenchymal cells, for stimulating the proliferation of neural precursor cells or endothelial cells,
 wherein the preparation is selected from one or both of a soluble-cell-free extract and an insoluble cell residue; and
 wherein the mesenchymal cells are descendants of MSCs that have been transiently transfected with a vector comprising sequences encoding a Notch intracellular domain (DNTT-MSCs).

19. The preparation of claim 18, further comprising a pharmaceutically acceptable carrier or excipient.

20. A preparation, from mesenchymal cells, for providing a mixture of FGF2 isoforms to a cell, tissue, or subject in need thereof;
 wherein the preparation is selected from one or both of a soluble-cell-free extract and an insoluble cell residue; and
 wherein the mesenchymal cells are descendants of MSCs that have been transiently transfected with a vector comprising sequences encoding a Notch intracellular domain (DNTT-MSCs).

21. The preparation of claim 20, wherein the cell is a neural precursor cell or an endothelial cell.

22. The preparation of claim 20, wherein the tissue comprises one or more of a neural precursor cell and/or an endothelial cell.

23. The preparation of claim 21, wherein proliferation of the neural precursor cell or the endothelial cell is induced.

24. The preparation of claim 22, wherein proliferation of the neural precursor cell or the endothelial cell is induced.

25. The preparation of claim 20, wherein the tissue or subject has undergone an ischemic injury.

26. The preparation of claim 25, wherein the ischemic injury is a stroke.

27. The preparation of claim 20, wherein the tissue is necrotic.

28. The preparation of claim 27, wherein necrosis results from infarction or traumatic injury.

29. The preparation of claim 20, further comprising a pharmaceutically acceptable carrier or excipient.

\* \* \* \* \*